US010485807B2

(12) United States Patent
Goldman et al.

(10) Patent No.: US 10,485,807 B2
(45) Date of Patent: Nov. 26, 2019

(54) MODULATING THE PRODUCTION OF NEURONS AND/OR OLIGODENDROCYTES FROM WHITE MATTER PROGENITOR CELLS

(71) Applicant: Cornell Research Foundation, Inc., Ithaca, NY (US)

(72) Inventors: Steven A. Goldman, Webster, NY (US); Fraser Sim, Batavia, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 15/352,249

(22) Filed: Nov. 15, 2016

(65) Prior Publication Data
US 2017/0119787 A1 May 4, 2017

Related U.S. Application Data

(63) Continuation of application No. 14/584,582, filed on Dec. 29, 2014, now abandoned, which is a continuation of application No. 12/368,838, filed on Feb. 10, 2009, now Pat. No. 8,945,921, which is a continuation of application No. 10/985,306, filed on Nov. 10, 2004, now abandoned.

(60) Provisional application No. 60/519,310, filed on Nov. 10, 2003.

(51) Int. Cl.
*C12N 5/00* (2006.01)
*A61P 25/28* (2006.01)
*A61K 31/555* (2006.01)
*A61K 31/737* (2006.01)
*G01N 33/68* (2006.01)

(52) U.S. Cl.
CPC .......... *A61K 31/555* (2013.01); *A61K 31/737* (2013.01); *G01N 33/6896* (2013.01); *G01N 2500/00* (2013.01); *G01N 2800/28* (2013.01)

(58) Field of Classification Search
None
See application file for complete search history.

(56) References Cited

U.S. PATENT DOCUMENTS 7,056,692 B2    6/2006  Deuel

OTHER PUBLICATIONS

Goldman et al (Science 338: 491-495, 2012) (Year: 2012).*
Patil et al (Drug Des Devel Ther 7: 729-745, 2013) (Year: 2013).*
Neuropathy, congenital hypomyelination <https://rarediseases.org/rare-diseases/neuropathy-congenital-hypomyelination/>, pp. 1-7, downloaded on May 28, 2018 (Year: 2018).*
Encephalitis—Wikipedia downloaded from <https://en.wikipedia.org/wiki/Encephalitis> on May 27, 2018, pp. 1-4. Last edited on May 22, 2018 (Year: 2018).*
Johnston et al (NeuroMol Med 8: 435-450, 2006) (Year: 2006).*
Agarwala et al., "Down Syndrome Cell Adhesion Molecule DSCAM Mediates Homophilic Intercellular Adhesion," *Brain Res. Mol. Brain Res.* 79:118-126 (2000).
Asher et al., "Versican is Upregulated in CNS Injury and is a Product of Oligodendrocyte Lineage Cells," *J. Neurosci.* 22(6):2225-2236 (2002).
Band & Posner, "Phosphatidylinositol 3'-Kinase and p70s6k Are Required for Insulin but Not Bisperoxovanadium 1,10-phenanthroline (bpV(phen)) Inhibition of Insulin-Like Growth Factor Binding Protein Gene Expression. Evidence for MEK-Independent Activation of Mitogen-Activated Protein Kinase by bpV(phen)," *J. Biol. Chem.* 272(1):138-145 (1997).
Bansal et al., "Developmental and FGF-2-Mediated Regulation of Syndecans (1-4) and Glypican in Oligodendrocytes," *Mol. Cell. Neurosci.* 7: 276-288 (1996b).
Bansal et al., "Regulation of FGF Receptors in the Oligodendrocyte Lineage," *Mol. Cell. Neurosci.* 7:263-275 (1996).
Bansal & Pfeiffer, "Regulation of Oligodendrocyte Differentiation by Fibroblast Growth Factors," *Adv. Exp. Med. Biol.* 429:69-77 (1997).
Bansal et al., "Specific Inhibitor of FGF Receptor Signaling: FGF-2-Mediated Effects on Proliferation, Differentiation, and MAPK Activation are Inhibited by PD173074 in Oligodendrocyte-Lineage Cells," *J. Neurosci. Res.* 74:486-93 (2003).
Barres et al., "A Novel Role for Thyroid Hormone, Glucocorticoids and Retinoic Acid in Timing Oligodendrocyte Development," *Development* 120:1097-1108 (1994).
Ben-Hur et al., "Growth and Fate of PSA-NCAM+ Precursors of the Postnatal Brain," *J. Neurosci.* 18 (15):5777-5788 (1998).
Bevan et al., "Selective Activation of the Rat Hepatic Endosomal Insulin Receptor Kinase. Role for the Endosome in Insulin Signaling," *J. Biol. Chem.* 270(18):10784-10791 (1995).
Canoll et al., "The Expression of a Novel Receptor-Type Tyrosine Phosphatase Suggests a Role in Morphogenesis and Plasticity of the Nervous System," *Brain Res. Dev. Brain Res.* 75:293-298 (1993).
Canoll et al., "Three Forms of RPTP-Beta are Differentially Expressed During Gliogenesis in the Developing Rat Brain and During Glial Cell Differentiation in Culture," *J. Neurosci. Res.* 44:199-215 (1996).
Chellaiah et al., "Fibroblast Growth Factor Receptor (FGFR) 3. Alternative Splicing in Immunoglobulin-Like Domain III Creates a Receptor Highly Specific for Acidic FGF/FGF-1," *J. Biol. Chem.* 269(15):11620-11627 (1994).

(Continued)

*Primary Examiner* — Gregory S Emch
*Assistant Examiner* — Aditi Dutt
(74) *Attorney, Agent, or Firm* — Pepper Hamilton LLP

(57) ABSTRACT

The present invention relates to a method of modulating production of neurons and/or oligodendrocytes from neural progenitor cells of human white matter and to a method of treating a subject for a condition modulated by underproduction of oligodendrocytes from human white matter. Both of these methods involve administering an agonist or antagonist of one or more molecules set forth in Tables 1 and/or 2 to the neural progenitor cells. Also disclosed is a method of using an inhibitor of sterol synthesis to differentiate oligodendrocyte progenitor cells to oligodendrocytes.

6 Claims, 3 Drawing Sheets

(56) References Cited

OTHER PUBLICATIONS

Chen et al, "Inhibition of Axon Growth by Oligodendrocyte Precursor Cells," *Mol. Cell. Neurosci.* 20:125-139 (2002).
Citron, et al., "Evidence that the 42- and 40-Amino Acid Forms of Amyloid β Protein are Generated from the β-Amyloid Precursor Protein by Different Protease Activities," *Proc. Natl. Acad. Sci. USA* 93:13170-75 (1996).
Curtis et al., "Down-regulation of GAP-43 During Oligodendrocyte Development and Lack of Expression by Astrocytes In Vivo: Implications for Macroglial Differentiation," *Eur. J. Neurosci.* 3:876-886 (1991).
De Strooper, et al., "A Presenilin-1-Dependent γ-Secretase-Like Protease Mediates Release of Notch Intracellular Domain," *Nature* 398:518-22 (1998).
Doerfler et al., "Presenilin-Dependent γ-Secretase Activity Modulates Thymocyte Development," *Proc. Natl. Acad. Sci. USA* 98(16):9312-17 (2001).
Dovey et al., "Functional Gamma-Secretase Inhibitors Reduce Beta-Amyloid Peptide Levels in Brain," *J. Neurochem.* 76:173-181 (2001).
Eisenbarth et al., "Monoclonal Antibody to a Plasma Membrane Antigen of Neurons," *Proc. Natl. Acad. Sci. USA* 76(10):4913-4917 (1979).
Engele et al., "Effects of Acidic and Basic Fibroblast Growth Factors (aFGF, bFGF) on Glial Precursor Cell Proliferation: Age Dependency and Brain Region Specificity," *Dev. Biol.* 152:363-372 (1992).
Fanarraga et al., "O-2A Progenitors of the Mouse Optic Nerve Exhibit A Developmental Pattern of Antigen Expression Different from the Rat," *Glia* 15:95-104 (1995).
Farrer & Quarles, "GT3 and its O-Acetylated Derivative are the Principal A2B5-Reactive Gangliosides in Cultured O2A Lineage Cells and are Down-Regulated Along with O-Acetyl GD3 During Differentiation to Oligodendrocytes," *J. Neurosci. Res.* 57:371-380 (1999).
Faure et al., "Arrest at the G2/M Transition of the Cell Cycle by Protein-Tyrosine Phosphatase Inhibition: Studies on a Neuronal and a Glial Cell Line," *J. Cell. Biochem.* 59:389-401 (1995).
Geling et al., "A γ-Secretase Inhibitor Blocks Notch Signaling in vivo and Causes a Severe Neurogenic Phenotype in Zebrafish," *EMBO Reports* 3(7):688-94 (2002).
Grinspan & Franceschini, "Platelet-Derived Growth Factor is a Survival Factor for PSA-NCAM+ Oligodendrocyte Pre-Progenitor Cells," *J. Neurosci. Res.* 41:540-551 (1995).
Gross et al., "Bone Morphogenetic Proteins Promote Astroglial Lineage Commitment by Mammalian Subventricular Zone Progenitor Cells," *Neuron* 17:595-606 (1996).
Grotewold et al., "Bambi is Coexpressed with Bmp-4 During Mouse Embryogenesis," *Mech. Dev.* 100:327-330 (2001).
Hachisuka et al., "Developmental Expression of Opioid-Binding Cell Adhesion Molecule (OBCAM) in Rat Brain," *Brain Res. Dev. Brain Res.* 122:183-191 (2000).
Hachisuka et al., "Localization of Opioid-Binding Cell Adhesion Molecule (OBCAM) in Adult Rat Brain," *Brain Res.* 842:482-486 (1999).
Hacohen et al., "Sprouty Encodes a Novel Antagonist of FGF Signaling That Patterns Apical Branching of the *Drosophila* Airways," *Cell* 92:253-263 (1998).
Hadeball et al., "Xenopus Cadherin-11 (Xcadherin-11) Expression Requires the Wg/Wnt Signal," *Mech. Dev.* 72:101-113 (1998).
Hadland et al., "γ-Secretase Inhibitors Repress Thymocyte Development," *Proc. Natl. Acad. Sci. USA* 98(13):7487-91 (2001).
Hamby et al., "Structure-Activity Relationships for a Novel Series of Pyrido[2,3-d]pyrimidine Tyrosine Kinase Inhibitors," *J. Med. Chem.* 40:2296-2303 (1997).
Hecht et al., "Identification of Fibroblast Growth Factor 9 (FGF9) as a High Affinity, Heparin Dependent Ligand for FGF Receptors 3 and 2 but not for FGF Receptors 1 and 4," *Growth Factors* 12:223-233 (1995).

Hillenbrand et al., "The Close Homologue of the Neural Adhesion Molecule L1 (CHL1): Patterns of Expression and Promotion of Neurite Outgrowth by Heterophilic Interactions," *Eur. J. Neurosci.* 11:813-826 (1999).
Hosack et al., "Identifying Biological Themes Within Lists of Genes with EASE," *Genome Biol.* 4:R70 (2003).
Hsueh et al., "Nuclear Translocation and Transcription Regulation by the Membrane-Associated Guanylate Kinase CASK/LIN-2," *Nature* 404:298-302 (2000).
Imai et al., "The Neural RNA-Binding Protein Musashi1 Translationally Regulates Mammalian Numb Gene Expression by Interacting With its mRNA," *Mol. Cell. Biol.* 21(12):3888-3900 (2001).
John et al., "Multiple Sclerosis: Re-Expression of a Developmental Pathway That Restricts Oligodendrocyte Maturation," *Nature Med* 8(10):1115-1121 (2002).
Jung et al., "Astrocytes and Neurons Regulate the Expression of the Neural Recognition Molecule Janusin by Cultured Oligodendrocytes," *Glia* 9:163-175 (1993).
Kilic et al., "Intracranial Inhibition of Platelet-derived Growth Factor-Mediated Glioblastoma Cell Growth by an Orally Active Kinase Inhibitor of the 2-Phenylaminopyrimidine Class," *Cancer Res.* 60:5143-50 (2000).
Kimura et al., "Expression of Cadherin-11 Delineates Boundaries, Neuromeres, and Nuclei in the Developing Mouse Brain," *Dev. Dyn.* 206:455-462 (1996).
Klafki et al., "The Carboxyl Termini of β-Amyloid Peptides 1-40 and 1-42 are Generated by Distinct γ-Secretase Activities," *J. Biol. Chem.* 271(45):28655-59 (1996).
Lee et al., "Characterization of a Brain-Specific Nuclear LIM Domain Protein (FHL1B) Which is an Alternatively Spliced Variant of FHL1," *Gene* 237:253-263 (1999).
Li et al., "A Retinoic Acid Synthesizing Enzyme in Ventral Retina and Telencephalon of the Embryonic Mouse," *Mech. Dev.* 95:283-289 (2000).
Li et al., "Insig-1 "Brakes" Lipogenesis in Adipocytes and Inhibits Differentiation of Preadipocytes," *Proc. Natl. Acad. Sci. USA* 100(16):9476-9481 (2003).
Li et al., "Pleiotrophin Gene Expression is Highly Restricted and is Regulated by Platelet-Derived Growth Factor," *Biochem. Biophys. Res. Commun.* 184(1):427-432 (1992).
Lu et al., "Sonic Hedgehog—Regulated Oligodendrocyte Lineage Genes Encoding bHLH Proteins in the Mammalian Central Nervous System," *Neuron* 25:317-29 (2000).
Mabie et al., "Bone Morphogenetic Proteins Induce Astroglial Differentiation of Oligodendroglial-Astroglial Progenitor Cells," *J. Neurosci.* 17(11):4112-4120 (1997).
Meng et al., "Pleiotrophin Signals Increased Tyrosine Phosphorylation of Beta-Catenin Through Inactivation of the Intrinsic Catalytic Activity of the Receptor-Type Protein Tyrosine Phosphatase Beta/Zeta," *Proc. Natl. Acad. Sci. USA* 97(6):2603-2608 (2000).
Milev et al., "High Affinity Binding and Overlapping Localization of Neurocan and Phosphacan/Protein-Tyrosine Phosphatase-Zeta/Beta With Tenascin-R, Amphoterin, and The Heparin-Binding Growth-Associated Molecule," *J. Biol. Chem.* 273(12):6998-7005 (1998).
Milev et al., "Interactions of the Chondroitin Sulfate Proteoglycan Phosphacan, the Extracellular Domain of a Receptor-Type Protein Tyrosine Phosphatase, With Neurons, Glia, and Neural Cell Adhesion Molecules," *J. Cell Biol.* 127(6):1703-1715 (1994).
Mohammadi et al., "Structures of the Tyrosine Kinase Domain of Fibroblast Growth Factor Receptor in Complex with Inhibitors," *Science* 276:955-60 (1997).
Molina-Holgado et al., "Cannabinoids Promote Oligodendrocyte Progenitor Survival: Involvement of Cannabinoid Receptors and Phosphatidylinositol-3 Kinase/Akt Signaling," *J. Neurosci.* 22(22):9742-9753 (2002).
Mosselman et al., "Developmentally Regulated Expression of Two Novel Platelet-Derived Growth Factor Alpha-Receptor Transcripts in Human Teratocarcinoma Cells," *Cancer Res.* 54:220-225 (1994).
Mueller et al., "Fibroblast Growth Factor Signaling Regulates Pillar Cell Development in the Organ of Corti," *J. Neurosci.* 22(21):9368-77 (2002).
Nagpal et al., "Tazarotene-Induced Gene 2 (TIG2), a Novel Retinoid-Responsive Gene in Skin," *J. Invest. Dermatol.* 109:91-95 (1997).

(56) References Cited

OTHER PUBLICATIONS

Nakajima et al., "Identification of Three Novel Non-Classical Cadherin Genes Through Comprehensive Analysis of Large cDNAs," *Brain Res. Mol. Brain Res.* 94:85-95 (2001).
Naruo et al., "Novel Secretory Heparin-Binding Factors From Human Glioma Cells (Glia-Activating Factors) Involved in Glial Cell Growth. Purification and Biological Properties," *J. Biol. Chem.* 268(4):2857-2864 (1993).
Niederost et al., "Bovine CNS Myelin Contains Neurite Growth-Inhibitory Activity Associated With Chondroitin Sulfate Proteoglycans," *J. Neurosci.* 19(20):8979-8989 (1999).
Noll & Miller, "Regulation of Oligodendrocyte Differentiation: A Role for Retinoic Acid in the Spinal Cord," *Development* 120:649-660 (1994).
Nunes et al., "Identification and Isolation of Multipotential Neural Progenitor Cells from the Subcortical White Matter of the Adult Human Brain," *Nat. Med.* 9:439-447 (2003).
O'Dowd et al., "A Novel Gene Codes for a Putative G Protein-Coupled Receptor with an Abundant Expression in Brain," *FEBS Lett.* 394:325-329 (1996).
Onichtchouk et al., "Silencing of TGF-Beta Signalling by the Pseudoreceptor BAMBI," *Nature* 401:480-485 (1999).
Ornitz et al., "Receptor Specificity of the Fibroblast Growth Factor Family," *J. Biol. Chem.* 271(25):15292-15297 (1996).
Peles et al., "Multi-ligand Interactions with Receptor-like Protein Tyrosine Phosphatase Beta: Implications for Intercellular Signaling," *Trends Biochem. Sci.* 23:121-124 (1998).
Pesheva et al., "Tenascin-R is an Intrinsic Autocrine Factor for Oligodendrocyte Differentiation and Promotes Cell Adhesion by a Sulfatide-Mediated Mechanism," *J. Neurosci.* 17(12):4642-4651 (1997).
Posner et al., "Peroxovanadium Compounds. A New Class of Potent Phosphotyrosine Phosphatase Inhibitors Which Are Insulin Mimetics," *J. Biol. Chem.* 269(6):4596-4604 (1994).
Raff, et al., "A Glial Progenitor Cell That Develops In Vitro Into an Astrocyte or an Oligodendrocyte Depending on Culture Medium," *Nature* 303:390-396 (1983).
Ramalho-Santos et al., ""Stemness": Transcriptional Profiling of Embryonic and Adult Stem Cells," *Science* 298:597-600 (2002).
Roth et al., "PPAR Gamma Activators Induce Growth Arrest and Process Extension in B12 Oligodendrocyte-like Cells and Terminal Differentiation of Cultured Oligodendrocytes," *J. Neurosci. Res.* 72:425-435 (2003).
Roy et al., "Identification, Isolation, and Promoter-defined Separation of Mitotic Oligodendrocyte Progenitor Cells From the Adult Human Subcortical White Matter," *J. Neurosci.* 19(22):9986-95 (1999).
Sakurai et al., "Induction of Neurite Outgrowth Through Contactin and Nr-CAM by Extracellular Regions of Glial Receptor Tyrosine Phosphatase Beta," *J. Cell Biol.* 136(4):907-918 (1997).
Sakuta et al., "Ventroptin: a BMP-4 Antagonist Expressed in a Double-Gradient Pattern in the Retina," *Science* 293:111-115 (2001).
Santos-Ocampo et al., "Expression and Biological Activity of Mouse Fibroblast Growth Factor-9," *J. Biol. Chem.* 271(3):1726-1731 (1996).
Sasaki et al, "Identification of a Dominant Negative Mutant of Sprouty That Potentiates Fibroblast Growth Factor—But Not Epidermal Growth Factor-Induced ERK Activation," *J. Biol. Chem.* 276(39):36804-36808 (2001).
Schmucker et al., "*Drosophila* Dscam is an Axon Guidance Receptor Exhibiting Extraordinary Molecular Diversity," *Cell* 101:671-684 (2000).
Schulz et al., "Syndecan 3 Intramembrane Proteolysis is Presenilin/Gamma—Secretase-Dependent and Modulates Cytosolic Signaling," *J. Biol. Chem.* 278(49):48651-57 (2003).
Seiffert et al., "Presenilin-1 and -2 are Molecular Targets for γ-Secretase Inhibitors," *J. Biol. Chem.* 275(44):34086-91 (2000).
Sever et al., "Accelerated Degradation of HMG CoA Reductase Mediated by Binding of Insig-1 to Its Sterol-sensing Domain," *Mol. Cell.* 11:25-33 (2003).
Shearman et al., "L-685,458, an Aspartyl Protease Transition State Mimic, is a Potent Inhibitor of Amyloid β-Protein Precursor γ-Secretase Activity," *Biochem.* 39:8698-704 (2000).
Shibata et al., "Identification of Human Cadherin-14, a Novel Neurally Specific Type II Cadherin, by Protein Interaction Cloning," *J. Biol. Chem.* 272(8):5236-5240 (1997).
Strehl et al., "Characterization of Two Novel Protocadherins (PCDH8 and PCDH9) Localized on Human Chromosome 13 and Mouse Chromosome 14," *Genomics* 53:81-89 (1998).
Takeuchi et al., "Expression of T-Cadherin (CDH13, H-Cadherin) in Human Brain and Its Characteristics as a Negative Growth Regulator of Epidermal Growth Factor in Neuroblastoma Cells," *J. Neurochem.* 74:1489-1497 (2000).
Tumbar et al., "Defining the Epithelial Stem Cell Niche in Skin," *Science* 303:359-363 (2004).
Uhrboom et al., "Dependence of Autocrine Growth Factor Stimulation in Platelet-Derived Growth Factor-B-Induced Mouse Brain Tumor Cells," *Int. J. Cancer* 85:398-406 (2000).
Walczak & Tontonoz, "PPARadigms and PPARadoxes: Expanding Roles for PPARgamma in the Control of Lipid Metabolism," *J. Lipid Res.* 43:177-186 (2002).
Wang et al., "Frzb, a Secreted Protein Expressed in the Spemann Organizer, Binds and Inhibits Wnt-8," *Cell* 88:757-766 (1997).
Wang et al., "Notch Receptor Activation Inhibits Oligodendrocyte Differentiation," *Neuron* 21:63-75 (1998).
Watanabe et al., "Transient Upregulation of Nkx2.2 Expression in Oligodendrocyte Lineage Cells During Remyelination," *Glia* 46:311-322 (2004).
Weber et al., "Mice Deficient for Tenascin-R Display Alterations of the Extracellular Matrix and Decreased Axonal Conduction Velocities in the CNS," *J. Neurosci.* 19(11):4245-4262 (1999).
Windrem et al., "Fetal and adult human oligodendrocyte progenitor cell isolates myelinate the congenitally dysmyelinated brain," *Nat. Med.* 10:93-97 (2004).
Winkler et al., "Syndecan-3 and Perlecan Are Differentially Expressed by Progenitors and Mature Oligodendrocytes and Accumulate in the Extracellular Matrix," *J. Neurosci. Res.* 69:477-487 (2002).
Wolfe et al., "Peptidomimetic Probes and Molecular Modeling Suggest that Alzheimer's γ-Secretase is an Intramembrane-Cleaving Aspartyl Protease," *Biochem.* 38:4720-27 (1999).
Yamakawa et al., "DSCAM: A Novel Member of the Immunoglobulin Superfamily Maps in a Down Syndrome Region and is Involved in the Development of the Nervous System," *Hum. Mol. Genet.* 7(2):227-237 (1998).
Yang et al., "Crucial Step in Cholesterol Homeostasis: Sterols Promote Binding of SCAP to INSIG-1, a Membrane Protein That Facilitates Retention of SREBPs in ER," *Cell* 110:489-500 (2002).
Yasuda et al., "Cloning and Chromosomal Mapping of the Human Gene of Neuroglycan C (NGC), a Neural Transmembrane Chondroitin Sulfate Proteoglycan with an EGF Module," *Neurosci. Res.* 32:313-322 (1998).
Zechner et al., "Beta-Catenin Signals Regulate Cell Growth and the Balance Between Progenitor Cell Expansion and Differentiation in the Nervous System," *Dev. Biol.* 258: 406-418 (2003).
Barral-Moran et al., "Oligodendrocyte Progenitor Migration in Response to Injury of Glial Monolayers Requires the Polysialic Neural Cell-Adhesion Molecule," *J. Neurosci. Res.* 72:679-690 (2003).
Cazillis et al., "In Vitro Induction of Neural Differentiation of Embryonic Stem (ES) Cells Closely Mimics Molecular Mechanisms of Embryonic Brain Development," *Ped. Res.* 59(4/Pt 2):48R-53R (2006).
Lee et al., "Fluvastatin and Lovastatin but Not Pravastatin Induce Neuroglial Differentiation in Human Mesenchymal Stem Cells," *J. Cell. Biochem.* 93:917-928.
Mujtaba et al., "A Common Neural Progenitor for the CNS and PNS," *Dev. Biol.* 200:1-15(1998).
Sim et al., "Complementary Patterns of Gene Expression by Human Oligodendrocyte Progenitors and Their Environment Predict Determinants of Progenitor Maintenance and Differentiation," *Ann. Neurol.* 59:763-779 (2006).

(56) References Cited

OTHER PUBLICATIONS

Windrem et al., "Progenitor Cells Derived from the Adult Human Subcortical White Matter Disperse and Differentiate as Oligodendrocytes Within Demyelinated Lesions of the Rat Brain," *J. Neurosci. Res.* 69:966-975 (2002).
Hsieh et al., "IGF-1 Instructs Multipotent Adult Neural Progenitor Cells to Become Oligodendrocytes," *J. Cell Bio.* 164(1):111-122 (2004).
Mabie et al., "Multiple Roles of Bone Morphogenetic Protein Signaling in the Regulation of Cortical Cell Number and Phenotype," *J. Neurosc.* 19(16):7077-7088 (1999).
McMahon et al., "Noggin-Mediated Antagonism of BMP Signaling is Required for Growth and Patterning of the Neural Tube and Somite," *Genes and Dev.* 12(10):1438-1452 (1998).
Mehler et al., "Developmental Changes in Progenitor Cell Responsiveness to Bone Morphogenetic Proteins Differentially Modulate Progressive CNS Lineage Fate," *Dev. Neurosc.* 22(1/2):74-85 (2000).
Harroch et al., Nature Gen 32:411-414 (2002).
Hawkins et al., Pharmacol Rev 57:173-185 (2005).
Zhao et al., J. Neurol Sci 233:87-91 (2005).
Comi et al., Clin Neurol and Neurosurg 108:339-345 (2006).
Said, Neuromus Disord 16:293-303 (2006).
Ranjan et al., Mol Cell Neurosci 7:404-418 (1996).
Kirschstein et al., Stem Cells, NIH, Jun. 2001, (pages from (2), Stem Cell Basics 1 of 4, 1 of 5).
Stangel, Expert Opin Invest Drugs 13:331-347 (2004).
Stangel, J Neurol Neurosurg Psychiat 72:1-4 (2002).
Deuel et al., Arch Biochem Biophys 297:162-171 (2002).
Posner et al., JBC 269:4596-4604 (1994).
Sakaguchi et al., Neurosci Res 45:219-224 (2003).
Marmur et al., Dev Biol 204:577-591 (1998).
Jakovcevski et al., Front Neuroanat 3:1-15 (2009).
Prenatal Diagnosis and Fetal Therapy, Updated May 11, 2016; article downloaded from http://emedicine.medscape.com.article/936318-overview, dated Jul. 30, 2016.
Lu et al., Exp. Neur. 178:259-267 (2002).

* cited by examiner

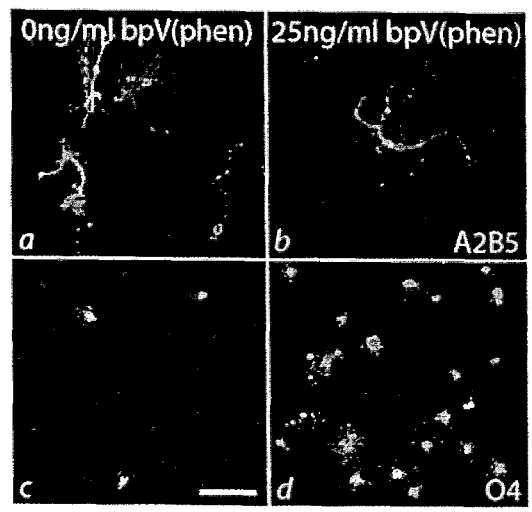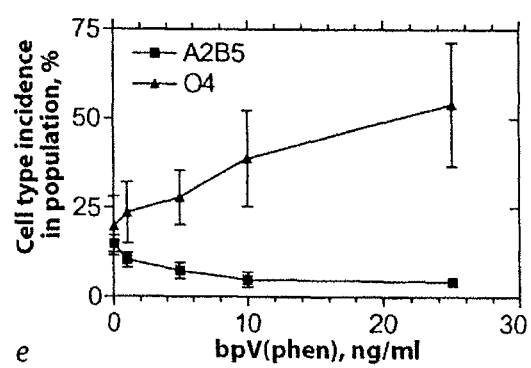
Figures 1A-E

Proposed Model of Statin effects on WMPCs

1. Statin treatment blocks HMGCR reducing intracellular cholesterol

2. Reduced cholesterol reduces INSIG1-SCAP binding leading to SREBP release

3. SREBP induces transcription of PPARγ

4. PPARγ stimulates WMPC oligodendrocytic differentiation

MODULATING THE PRODUCTION OF NEURONS AND/OR OLIGODENDROCYTES FROM WHITE MATTER PROGENITOR CELLS

This application is a continuation of U.S. Patent application Ser. No. 14/584,582, filed Dec. 29, 2014, now abandoned, which is a continuation of U.S. patent application Ser. No. 12/368,838, filed Feb. 10, 2009, now U.S. Pat. No. 8,945,921, issued Feb. 3, 2015, which is a continuation of U.S. patent application Ser. No. 10/985,306, filed Nov. 10, 2004, now abandoned, which claims the benefit of U.S. Provisional Patent Application Ser. No. 60/519,310, filed Nov. 10, 2003, each of which is hereby incorporated by reference in its entirety.

This invention was made with government support under R01NS33106 and R01NS39559 awarded by NINDS. The government has certain rights in the invention.

FIELD OF THE INVENTION

The present invention is directed to genes differentially expressed by acutely isolated resident progenitor cells of the human white matter.

BACKGROUND OF THE INVENTION

An abundant population of glial progenitor cells resides in the adult human subcortical white matter. These cells give rise to myelinogenic oligodendrocytes upon transplantation, yet when removed from the tissue environment they behave as multipotential neurogenic progenitors. To identify genes that regulate their homeostasis and cell fate decisions of these adult progenitor cells, the transcriptional profile of A2B5$^+$ white matter progenitor cells (WMPCs) sorted from human surgical resections. The profile of each progenitor isolate sorted cell population was then normalized against that of the tissue white matter from which it was derived to identify progenitor-enriched transcripts. WMPCs expressed high levels of PDGFaR, GD3 synthase and NG2 prototypic oligodendrocyte progenitor genes, yet they also expressed high levels of MASH1 and HES1, suggesting a more primitive phenotype. RNAs encoding the members of several parallel signaling pathways were differentially expressed by WPMCs relative to unsorted cells. These included receptor tyrosine phosphate (RTP)-β/ζ, its ligand pleiotrophin, and its modulators NrCAM, tenascin R, and the chondroitin sulfate proteoglycans (CSPG2-5); PDGFαR, which induces pleiotrophin; syndecan-3, its membrane partner FGFR3, and its intracellular partner CASK; the BMP inhibitors neuralin and BAMBI; and the notch intermediates HES1, musashi and FHL1B. When exposed to oxovanadate, an RTP inhibitor, WMPCs ceased expansion and differentiated as oligodendrocytes, validating the central role of RTP-β/ζ in progenitor self-maintenance. The co-activation of RTP-β/ζ with these interactive parallel pathways may provide the means by which adult progenitors are maintained in a multipotential and mitotically-competent state. As such, they may provide targets by which to perturb cell fate choices by progenitor cells of the adult human brain.

A population of nominally glial progenitor cells resides in the parenchyma of the adult human subcortical white matter. These cells may be defined by A2B5-immunoreactivity, and by their expression of fluorescent reporters placed under the control of the CNP2 promoter (Roy et al., "Identification, Isolation, and Promoter-defined Separation of Mitotic Oligodendrocyte Progenitor Cells From the Adult Human Subcortical White Matter." *J Neurosci* 19: 9986-95 (1999); Nunes et al., "Identification and Isolation of Multipotential Neural Progenitor Cells from the Subcortical White Matter of the Adult Human Brain." *Nat Med* 9: 439-447 (2003)). The cells typically act as oligodendrocyte progenitors, giving rise to myelinogenic oligodendrocytes upon transplantation. However, when removed from the tissue environment, they behave as multipotential and neurogenic progenitor cells. This observation suggested that the local tissue environment regulates both the self-renewal and phenotype of parenchymal glial progenitors, such that the latter actually represent a pool of multipotential progenitors whose fate is tonically restricted by their local tissue environment. As a result, the environmental cues presented to these cells, and their responsiveness to these signals, may determine not only their mitotic turnover, but also their undifferentiated self-renewal and post-mitotic lineage choices. Yet no studies to date have specifically examined the environment of the adult human white matter from the standpoint of steady-state cues and cell-specific responsiveness by resident progenitor cells.

The present invention is directed to overcoming this deficiency in the art.

SUMMARY OF THE INVENTION

The present invention relates to a method of modulating production of neurons and/or oligodendrocytes from neural progenitor cells of human white matter. This involves administering an agonist or antagonist of one or more molecules set forth in Tables 1 and/or 2 to the neural progenitor cells under conditions effective to modulate production of neurons and/or oligodendrocytes.

Another aspect of the present invention relates to a method of treating a subject for a condition modulated by underproduction, dysfunction, or loss of oligodendrocytes from human white matter. This method involves administering to the subject an agonist or antagonist of one or more molecules set forth in Tables 1 and/or 2 under conditions effective to treat the condition modulated by underproduction, dysfunction, or loss of oligodendrocytes.

Another aspect of the present invention relates to a method differentiating oligodendrocyte progenitor cells to oligodendrocytes. This involves administering an inhibitor of sterol synthesis under conditions effective to differentiate oligodendrocyte progenitor cells to oligodendrocytes.

To identify genes that regulate both the turnover and fate decisions of adult glial progenitor cell population in vivo, U95Av2 Affymetrix microarrays were used to analyze the transcriptional profile of A2B5$^+$ white matter progenitor cells (WMPCs), sorted from human white matter samples derived from surgically-resected adult temporal lobe. The profile of each sorted cell population was then normalized against that of the unsorted dissociate from which it was derived, to identify WMPC-enriched transcripts that were otherwise under-represented in the white matter. By this strategy, several unexpected ligands and receptors and their attendant signaling pathways were identified that appear to uniquely characterize the interaction of oligodendrocyte progenitor cells with the ambient white matter in which they reside.

BRIEF DESCRIPTION OF THE DRAWINGS

FIGS. 1A-E show tyrosine phosphatase inhibition induces oligodendrocyte differentiation by adult WMPCs. As shown in FIGS. 1A-D, WMPCs were treated with 0 or 25 ng/ml bpV(phen) for 7 days in vitro; matched wells were then stained for either A2B5 or O4. FIG. 1E shows the dose response curve of the percentage of A2B5$^+$ or O4$^+$ cells as a function of bpV(phen) dose (±SEM, n=4). Scale bar, 10 μM.

DETAILED DESCRIPTION OF THE INVENTION

Figure 2:
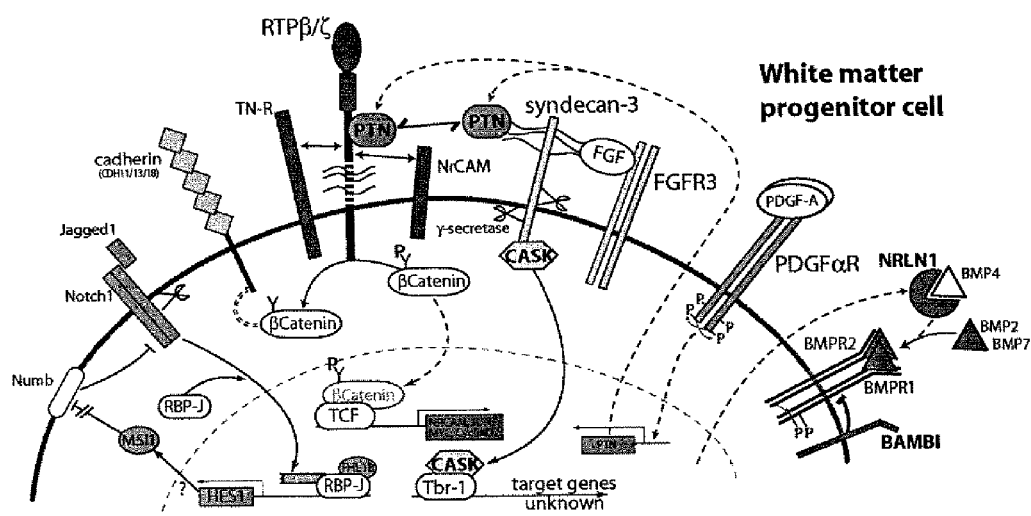
FIG. 2 shows the signal pathways identified within the adult human WMPC. Over 110 specific genes were significantly and differentially expressed by isolated human WMPCs. The assignment of these genes into coherent signaling pathways allowed generation of this model, which may predict aspects of the metabolic regulation of WMPCs at steady state, in the adult white matter environment. The signaling pathways predominant in this model are pleiotrophin signaling via RTPβ/ζ or syndecan-3, notch signaling, PDGFαR-dependent signaling, and BMP signaling and inhibition thereof. Genes in color were found to be significantly enriched in white matter progenitors, compared to unsorted white matter cells.

The present invention relates to a method of modulating production of neurons and/or oligodendrocytes from neural progenitor cells of human white matter. This involves administering an agonist or antagonist of one or more molecules set forth in Tables 1 and/or 2 to the neural progenitor cells under conditions effective to modulate production of neurons and/or oligodendrocytes.

TABLE 1

Genes Enriched in A2B5-sorted Adult Human WMPCs Compared to Unsorted Dissociate

| | LIGANDS, ANTAGONISTS & SECRETED PROTEINS | | | |
|---|---|---|---|---|
| BMP2 | Dpp homologue | | CHGB | chromogranin B (secretogranin 1) |
| BMP7 | OP-1 | | CLU | clusterin |
| FRZB | SFRP3 | | MMP16 | matrix metalloproteinase 16 (membrane-inserted) |
| NELL1 | NEL-like 1 (chicken), NRP1 | | PRSS11 | protease, serine, 11 (IGF binding) |
| NELL2 | NEL-like 2 (chicken), NRP2 | | SCG2 | secretogranin II (chromogranin C) |
| NRLN1 | Neuralin 1 | | SERPINE2 | glia-derived nexin |
| PTN | pleiotrophin | | TIMP4 | tissue inhibitor of metalloproteinase 4 |
| SLIT1 | slit homolog 1 (*Drosophila*) | | | |
| | RECEPTORS & DOWNSTREAM COMPONENTS | | | |
| CNR1 | cannabinoid receptor 1 (brain) | | ACK1 | activated p21cdc42Hs kinase |
| FGFR3 | fibroblast growth factor receptor 3 | | ADCY8 | adenylate cyclase 8 (brain), ADCY3, HBAC1 |
| GABBR1 | gamma-aminobutyric acid (GABA) B receptor, 1 | | ARHGEF4 | Rho guanine nucleotide exchange factor (GEF) 4 |
| GABRB1 | GABA A receptor | | ARHGEF6 | Rac/Cdc42 guanine nucleotide exchange factor (GEF) 6 |
| GLRB | glycine receptor, beta | | ARL7 | ADP-ribosylation factor-like 7 |
| GPR19 | G protein-coupled receptor 19 | | CAP2 | adenylyl cyclase-associated protein 2 |
| GRIA2 | glutamate receptor, ionotropic, AMPA 2 | | CASK | calcium/calmodulin-dependent serine protein kinase |
| GRIA3 | glutamate receptor, ionotrophic, AMPA 3 | | DOK5 | docking protein 5 |
| GRIK1 | glutamate receptor, ionotropic, kainate 1 | | INSIG1 | insulin induced gene 1 |
| GRIK2 | glutamate receptor, ionotropic, kainate 2 | | JIK | STE20-like kinase |
| KLRC3 | killer cell lectin-like receptor subfamily C, member 3 | | MAB21L1 | mab-21-like 1 |
| LDLR | low density lipoprotein receptor | | MAGED1 | NRAGE, DLXIN1 |
| LRP1 | low density lipoprotein-related protein 1 (alpha-2-macroglobulin receptor) | | NMA | BAMBI |
| PDGFRA | platelet-derived growth factor receptor, alpha polypeptide | | PKIA | protein kinase (cAMP-dependent, catalytic) inhibitor alpha |
| TM4SF2 | transmembrane 4 superfamily member 2 | | PPAP2B | phosphatidic acid phosphatase type 2B |
| TM4SF6 | transmembrane 4 superfamily member 6 | | RAB31 | RAB31, member RAS oncogene family |
| | | | SHC3 | neuronal Shc |
| | | | SIAH1 | seven in absentia homolog 1 (*Drosophila*) |
| | | | SPRY2 | sprouty homolog 2 (*Drosophila*) |
| | CELL ADHESION & EXTRACELLULAR MATRIX MOLECULES | | | |
| ASTN | astrotactin | | PCDH8 | protocadherin 8, PAPC, Arcadlin |
| CDH11 | OB-Cadherin | | SDC3 | syndecan 3 (N-syndecan) |
| CDH13 | cadherin 13, H-cadherin (heart) | | BGN | biglycan |
| CDH18 | cadherin 18, type 2 | | COL11A1 | collagen, type XI, alpha 1 |
| CHL1 | close homolog of L1CAM | | COL16A1 | collagen, type XVI, alpha 1 |
| CLDN10 | claudin 10 | | CRTL1 | cartilage linking protein 1 |
| CLSTN1 | calsyntenin 1 | | CSPG2 | versican |
| DSCAM | Down syndrome cell adhesion molecule | | CSPG3 | neurocan |
| FLRT2 | fibronectin leucine rich transmembrane protein 2 | | CSPG4 | NG2 |
| GPM6A | glycoprotein M6A | | CSPG5 | neuroglycan C/NGC |
| ITGA7 | integrin, alpha 7 | | PTPRZ1 | RPTPzeta/phosphocan |
| KIAA1775 | MT-protocadherin | | SPARCL1 | SPARC-like 1 (mast9, hevin) |
| NCAM1 | NCAM | | THBS2 | thrombospondin 2 |
| NLGN1 | neuroligin 1 | | THBS4 | thrombospondin 4 |
| NRCAM | neuronal cell adhesion molecule | | TNR | tenascin-R |
| OPCML | OBCAM | | | |

TABLE 1-continued

Genes Enriched in A2B5-sorted Adult Human WMPCs Compared to Unsorted Dissociate

ENZYMES

| | | | |
|---|---|---|---|
| ALDH1A3 | aldehyde dehydrogenase 1 family, member A3 | IDI1 | isopentenyl-diphosphate delta isomerase |
| ALDH5A1 | aldehyde dehydrogenase 5 family, member A1 (succinate-semialdehyde dehydrogenase) | KIAA0455 | PLASTICITY-RELATED GENE 1/PRG1 |
| ALDOC | Zebrin II/Aldolase C | LCK | lymphocyte-specific protein tyrosine kinase, p56(lck) |
| B3GNT6 | IGAT, IGNT, iGAT, iGNT, BETA3GNTI | MOXD1 | monooxygenase, DBH-like 1 |
| BAAT | bile acid Coenzyme A: amino acid N-acyltransferase (glycine N-choloyltransferase) | NME4 | non-metastatic cells 4, protein expressed in |
| CHST10 | carbohydrate sulfotransferase 10 | PDE8B | phosphodiesterase 8B |
| CKMT1 | creatine kinase, mitochondrial 1 (ubiquitous) | PFKM | phosphofructokinase, muscle |
| CPE | carboxypeptidase E | PGM1 | phosphoglucomutase 1 |
| DUSP8 | dual specificity phosphatase 8 | PRDX2 | peroxiredoxin 2 |
| ELOVL5 | ELOVL family member 5, elongation of long chain fatty acids (FEN1/Elo2, SUR4/Elo3-like, yeast) | PTPN4 | protein tyrosine phosphatase, non-receptor type 4 (megakaryocyte) |
| GAD1 | GAD67 | SC4MOL | sterol-C4-methyl oxidase-like |
| GLDC | glycine dehydrogenase (glycine cleavage system protein P) | SIAT8A | GD3 synthase |
| H105E3 | NAD(P) dependent steroid dehydrogenase-like | TRB2 | tribbles homolog 2 |
| HMGCR | HMG-CoA; 3-hydroxy-3-methylglutaryl-Coenzyme A reductase | | |

TRANSCRIPTION FACTORS & REGULATORS

| | | | |
|---|---|---|---|
| ASCL1 | MASH1 | LHX2 | LIM homeobox protein 2, LH-2 |
| CROC4 | transcriptional activator of the c-fos promoter | NFIB | nuclear factor I/B |
| FHL1 | SLIM1 | NR2F1 | COUP-TFI |
| FOXG1B | BF1 | NRF | NF-kappa B-repressing factor |
| HCFC1 | host cell factor C1 | SOX13 | SRY (sex determining region Y)-box 13 |
| HES1 | hairy and enhancer of split 1 | SOX4 | SRY (sex determining region Y)-box 4 |
| HLF | hepatic leukemia factor | SOX5 | SRY (sex determining region Y)-box 5 |
| ING3 | inhibitor of growth family, member 3 | ZFP36L2 | zinc finger protein 36, C3H type-like 2 |
| JUN | c-JUN | | |

OTHER GENES

| | | | |
|---|---|---|---|
| ABCC8 | ATP-binding cassette, sub-family C (CFTR/MRP), member 8 | LPHN3 | latrophilin 3 |
| ACCN2 | amiloride-sensitive cation channel 2, neuronal | MAP2 | microtubule-associated protein 2 |
| ACTC | actin, alpha, cardiac muscle | MEG3 | maternally expressed 3 |
| AF1Q | ALL1-fused gene from chromosome 1q | MID1 | midline 1 (Opitz/BBB syndrome) |
| APOD | apolipoprotein D | N33 | Putative prostate cancer tumor suppressor |
| ATP1A2 | ATPase, Na+/K+ transporting, alpha 2 | NCALD | neurocalcin delta |
| ATP1B2 | ATPase, Na+/K+ transporting, beta 2 polypeptide | NEBL | nebulette |
| ATP2A2 | ATPase, Ca++ transporting, cardiac muscle, slow twitch 2 | NICE-4 | NICE-4 protein |
| ATP2B4 | ATPase, Ca++ transporting, plasma membrane 4 | NPD009 | NPD009 protein |
| BASP1 | brain abundant, membrane attached signal protein 1 | NPIP | nuclear pore complex interacting protein |
| BC008967 | hypothetical gene | OIP106 | OGT(O-Glc-NAc transferase)-interacting protein 106 Kda |
| BSCL2 | Bernardinelli-Seip congenital lipodystrophy 2 (seipin) | OLFM1 | olfactomedin 1 |
| C11orf8 | chromosome 11 open reading frame 8 | PARD3 | par-3 partitioning defective 3 homolog |
| CADPS | Ca2+-dependent activator protein for secretion | PCF11 | PCF11p homolog |
| CCND1 | cyclin D1 (PRAD1: parathyroid adenomatosis 1) | PDE4DIP | phosphodiesterase 4D interacting protein (myomegalin) |
| COG4 | component of oligomeric golgi complex 4 | PDZK3 | PDZ domain containing 3 |
| CRMP1 | DRP1, DPYSL1, ULIP3 | PER1 | period homolog 1 (*Drosophila*) |
| CRY1 | cryptochrome 1 | PER2 | period homolog 2 (*Drosophila*) |
| D2S448 | Melanoma associated gene | PM5 | pM5 protein |
| DCX | doublecortin | PNMA2 | paraneoplastic antigen MA2 |
| DNAJB1 | HSP40 | ProSAPiP1 | ProSAPiP1 protein |
| DPYSL3 | DRP3, CRMP4, ULIP1 | RAMP1 | receptor (calcitonin) activity modifying protein 1 |
| DZIP1 | zinc finger DAZ interacting protein 1 | RARRES2 | retinoic acid receptor responder (tazarotene induced) 2 |
| EEF1A2 | eukaryotic translation elongation factor 1 alpha 2 | RBBP6 | retinoblastoma binding protein 6 |
| EMU1 | emilin and multimerin-domain containing protein 1 | SCRG1 | scrapie responsive protein 1 |
| EPM2AIP1 | EPM2A (laforin) interacting protein 1 | SEMA5A | sema domain, seven thrombospondin repeats (type 1 and type 1-like), transmembrane domain (TM) and short cytoplasmic domain, (semaphorin) 5A |
| EPN2 | epsin 2 | SEMACAP3 | likely ortholog of mouse semaF cytoplasmic domain associated protein 3 |
| F3 | coagulation factor III, TF | SEZ6L | seizure related 6 homolog (mouse)-like |
| FLJ13310 | hypothetical protein FLJ13310 | SLC1A1 | solute carrier family 1 (neuronal/epithelial high affinity glutamate transporter, system Xag), member 1 |

TABLE 1-continued

Genes Enriched in A2B5-sorted Adult Human WMPCs Compared to Unsorted Dissociate

| | | | |
|---|---|---|---|
| GAP43 | growth associated protein 43 | SLC1A2 | glial high affinity glutamate transporter |
| HIS1 | HMBA-inducible, CLP1, HIS1 | SMARCD3 | SWI/SNF related, matrix associated, actin dependent regulator of chromatin, subfamily d, member 3 |
| HSPH1 | HSP105A, HSP105B | SRPX | sushi-repeat-containing protein, X chromosome |
| ITM2A | integral membrane protein 2A | SYT11 | synaptotagmin XI |
| KCNB1 | potassium voltage-gated channel, Shab-related subfamily, member 1 | TARBP1 | TAR (HIV) RNA binding protein 1 |
| KCND3 | potassium voltage-gated channel, Shal-related subfamily, member 3 | THY1 | Thy-1 cell surface antigen |
| KIAA0062 | KIAA0062 protein | TNKS | tankyrase, TRF1-interacting ankyrin-related ADP-ribose polymerase |
| KIAA0354 | KIAA0354 gene product | TRB@ | T cell receptor beta locus |
| KIAA0888 | KIAA0888 protein | TRIM9 | tripartite motif-containing 9 |
| KIAA0931 | KIAA0931 protein | TRO | trophinin, magphinin, MAGED3 |
| KIAA0992 | Palladin | TUBB | tubulin, beta polypeptide |
| LAPTM4B | lysosomal associated protein transmembrane 4 beta | USP24 | ubiquitin specific protease 24 |
| LOC348155 | similar to hypothetical protein LOC283824 | YAF2 | YY1 associated factor 2 |
| LOH11CR2A | loss of heterozygosity, 11, chromosomal region 2, gene A | | |

Matched profiles of A2B5-sorted WMPCs and the tissue dissociate from a single white matter sample were compared against one another. Significantly enriched genes were identified using the resulting expression ratios. Expression of reliably detected genes, those with at least one present call, were analyzed. Over 250 probes sets were identified that possessed significantly enriched expression in the WMPCs, i.e. significantly different ratios compared to unity as determined by a pairwise t-test, $p < 0.05$, with 20% FDR multiple testing correction. These probe sets were annotated to 210 distinct genes, shown here. These genes were annotated using LocusLink, OMIM, and PubMed to assertain possible function in WMPC regulation.

TABLE 2

Genes Depleted from A2B5-sorted Adult Human WMPCs Compared to Unsorted Dissociate

| LIGANDS, ANTAGONISTS & SECRETED PROTEINS | | | |
|---|---|---|---|
| CCL20 | chemokine (C-C motif) ligand 20 | IL1B | interleukin 1, beta |
| FGF1 | acidic FGF | IL1RN | interleukin 1 receptor antagonist |
| GRN | granulin | | |

| RECEPTORS & DOWNSTREAM COMPONENTS | | | |
|---|---|---|---|
| C3AR1 | complement component 3a receptor 1 | CCRL2 | chemokine (C-C motif) receptor-like 2 |
| FCGR2A | Fc fragment of IgG, low affinity IIa, receptor for (CD32) | DOK1 | docking protein 1, 62 kDa (downstream of tyrosine kinase 1) |
| IL10RA | interleukin 10 receptor, alpha | LYN | v-yes-1 Yamaguchi sarcoma viral related oncogene homolog |
| LILRB4 | leukocyte immunoglobulin-like receptor, subfamily B (with TM and ITIM domains), member 4 | MPP1 | membrane protein, palmitoylated 1, 55 kDa |
| CCR1 | chemokine (C-C motif) receptor 1 | SOCS4 | suppressor of cytokine signaling 4 |
| CCR5 | chemokine (C-C motif) receptor 5 | | |

| ENZYMES | | | |
|---|---|---|---|
| BLVRB | biliverdin reductase B (flavin reductase (NADPH)) | LIPA | lipase A, lysosomal acid, cholesterol esterase (Wolman disease) |
| GPX1 | glutathione peroxidase 1 | MEP1A | meprin A, alpha (PABA peptide hydrolase) |
| GSTO1 | glutathione S-transferase omega 1 | PTP4A2 | protein tyrosine phosphatase type IVA, member 2 |
| KYNU | kynureninase (L-kynurenine hydrolase) | | |

| TRANSCRIPTION FACTORS & REGULATORS | | | |
|---|---|---|---|
| HIF1A | hypoxia-inducible factor 1, alpha subunit (basic helix-loop-helix transcription factor) | PPARG | PPAR gamma |
| TFEC | transcription factor EC | | |

| OTHER GENES | | | |
|---|---|---|---|
| CLIC1 | chloride intracellular channel 1 | HLA-DPA1 | major histocompatibility complex, class II, DP alpha 1 |
| FER1L3 | fer-1-like 3, myoferlin (C. elegans) | HLA-DQB1 | major histocompatibility complex, class II, DQ beta 1 |
| KIAA0053 | KIAA0053 gene product | HLA-DRB1 | major histocompatibility complex, class II, DR beta 1 |
| LOC253982 | hypothetical protein LOC253982 | KIF1C | kinesin family member 1C |
| LPXN | leupaxin | LCP1 | lymphocyte cytosolic protein 1 (L-plastin) |
| LY86 | lymphocyte antigen 86 | LCP2 | lymphocyte cytosolic protein 2 (SH2 domain containing leukocyte protein of 76 kDa) |
| TRIM44 | tripartite motif-containing 44 | LGALS1 | lectin, galactoside-binding, soluble, 1 (galectin 1) |

TABLE 2-continued

Genes Depleted from A2B5-sorted Adult Human WMPCs Compared to Unsorted Dissociate

| APOC2 | apolipoprotein C-II | PXR1 | peroxisome receptor 1 |
| --- | --- | --- | --- |
| BCL2L2 | BCL2-like 2 | RNASE6 | ribonuclease, RNase A family, k6 |
| FABP4 | fatty acid binding protein 4, adipocyte | S100A11 | S100 calcium binding protein A11 (calgizzarin) |
| GAS7 | growth arrest-specific 7 | TRIM38 | tripartite motif-containing 38 |
| HBA1 | hemoglobin, alpha 1 | UCP2 | uncoupling protein 2 (mitochondrial, proton carrier) |
| HBG1 | hemoglobin, gamma A | | |

Matched profiles of A2B5-sorted WMPCs and the tissue dissociate from a single white matter sample were compared against one another. Significantly depleted genes were identified using the resulting expression ratios. Expression of reliably detected genes, those with at least one present call, were analyzed. 51 probes sets were identified that possesed significantly lower expression in the WMPCs than the tissue dissociate, i.e. significantly different ratios compared to unity as determined by a pairwise t-test, p < 0.05, with 20% FDR multiple testing correction. These probe sets were annotated to 51 distinct genes, shown here. These genes were annotated using LocusLink, OMIM, and PubMed to assertain possible function in WMPC regulation.

Agonists and antagonists in accordance with the present invention are well known to those skilled in the art.

Examples of gamma-secretase inhibitors include: L-685, 458 (Shearman, et. al., "L-685,458, an Aspartyl Protease Transition State Mimic, is a Potent Inhibitor of Amyloid β-Protein Precursor γ-Secretase Activity," Biochem. 39:8698-704 (2000); Doerfler, et. al., "Presenilin-Dependent γ-Secretase Activity Modulates Thymocyte Development," Proc. Nat'l Acad. Sci USA 98(16): 9312-17 (2001), which are hereby incorporated by reference in their entirety); MG132 (Klafki, et. al., "The Carboxyl Termini of β-Amyloid Peptides 1-40 and 1-42 are Genereated by Distinct γ-Secretase Activities," J. Biol. Chem. 271(45): 28655-59 (1996); Strooper, et. al., "A Presenilin-1-Dependent γ-Secretase-Like Protease Mediates Release of Notch Intracellular Domain," Nature 398:518-22 (1998), which are hereby incorporated by reference in their entirety), Compounds A-G in Seiffert, et. al., "Presenilin-1 and -2 are Molecular Targets for γ-Secretase Inhibitors," J. Biol. Chem. 275(44): 34086-91 (2000), which is hereby incorporated by reference in its entirety; compounds-2 and -3 in Doerfler, et. al., "Presenilin-Dependent γ-Secretase Activity Modulates Thymocyte Development," Proc. Nat'l Acad. Sci USA 98(16): 9312-17 (2001), which is hereby incorporated by reference; MD28170 (Citron, et. al., "Evidence that the 42- and 40-Amino Acid Forms of Amyloid β Brotein are Generated from the β-Amyloid Precursor Protein by Different Protease Activities," Proc. Nat'l Acad. Sci. USA 93: 13170-75 (1996); De Strooper, et. al., "A Presenilin-1-Dependent γ-Secretase-Like Protease Mediates Release of Notch Intracellular Domain," Nature 398:518-22 (1998), which are hereby incorporated by reference in their entirety); difluoro ketone compound CM115 (Wolfe, et. al., "Peptidomimetic Probes and Molecular Modeling Suggest that Alzheimer's γ-Secretase is an Intramembrane-Cleaving Aspartyl Protease," Biochem. 38:4720-27 (1999), which is hereby incorporated by reference in its entirety); MW167 (De Strooper, et. al., "A Presenilin-1-Dependent γ-Secretase-Like Protease Mediates Release of Notch Intracellular Domain," Nature 398:518-22 (1998); Wolfe, et. al., "Peptidomimetic Probes and Molecular Modeling Suggest that Alzheimer's γ-Secretase is an Intramembrane-Cleaving Aspartyl Protease," Biochem. 38:4720-27 (1999), which are hereby incorporated by reference in their entirety); CM115 (Wolfe, et. al., "Peptidomimetic Probes and Molecular Modeling Suggest that Alzheimer's γ-Secretase is an Intramembrane-Cleaving Aspartyl Protease," Biochem. 38:4720-27 (1999); Hadland, et. al., "γ-Secretase Inhibitors Repress Thymocyte Development," Proc. Nat'l Acad. Sci. USA 98(13): 7487-91 (2001) (compound 11)), which are hereby incorporated by reference in their entirety); DAPT or N—[N-(3,5-difluoro-phenacetyl)-L-alanyl]-S-phenylglycine t-butyl ester (Dovey, et. al., "Functional Gamma-Secretase Inhibitors Reduce Beta-Amyloid Peptide Levels in Brain," J. Neurochem. 76: 173-81 (2001); Geling, et. al., "A γ-Secretase Inhibitor Blocks Notch Signaling in vivo and Causes a Severe Neurogenic Phenotype in Zebrafish," EMBO Reports 3(7): 688-94 (2002), which are hereby incorporated by reference in their entirety); and various γ-secretase inhibitors in the Calbiochem Catalog as follows:

| Cat. No. | Product Name |
| --- | --- |
| 101500 | AEBSF, Hydrochloride |
| 171601 | APP β-Secretase Inhibitor |
| 196000 | Bafilomycin A1, Streptomyces griseus |
| 496000 | OM99-2 |
| 516485 | Pepstatin A Methyl Ester |
| 565777 | γ-Secretase Inhibitor XVI |
| 565749 | β-Secretase Inhibitor II |
| 565780 | β-Secretase Inhibitor III |
| 565750 | γ-Secretase Inhibitor I |
| 565755 | γ-Secretase Inhibitor II |
| 565760 | γ-Secretase Inhibitor III |
| 565761 | γ-Secretase Inhibitor IV |
| 565762 | γ-Secretase Inhibitor V |
| 565763 | γ-Secretase Inhibitor VI |
| 565770 | γ-Secretase Inhibitor IX (DAPT, see above) |
| 565771 | γ-Secretase Inhibitor X (L-685, 458, see above) |
| 565772 | γ-Secretase Inhibitor XI |
| 565773 | γ-Secretase Inhibitor XII |
| 565774 | γ-Secretase Inhibitor XIII |
| 565775 | γ-Secretase Inhibitor XIV |
| 565778 | γ-Secretase Inhibitor XVII |
| 565779 | γ-Secretase Inhibitor XVIII |
| 565765 | $\gamma_{40}$-Secretase Inhibitor I |
| 565766 | $\gamma_{40}$-Secretase Inhibitor II |
| 565787 | γ-Secretase Inhibitor XIX |

Examples of FGFR3 inhibitors include: PD1703074 (Bansal, et. al., "Specific Inhibitor of FGF Receptor Signaling: FGF-2-Mediated Effects on Proliferation, Differentiation, and MAPK Activation are Inhibited by PD173074 in Oligodendrocyte-Lineage Cells," J. Neurosci. Res. 74: 486-93 (2003) and Hamby, et. al., "Structure-Activity Relationships for a Novel Series of Pyrido[2,3-d]pyrimidine Tyrosine Kinase Inhibitors," J. Med. Chem. 40:2296-303 (1997) (compound 4e), which are hereby incorporated by reference in their entirety) and SU5402 (Mohammadi, et. al., "Structures of the Tyrosine Kinase Domain of Fibroblast Growth Factor Receptor in Complex with Inhibitors," Science 276: 955-60 (1997) and Mueller, et. al., "Fibroblast Growth Factor Signaling Regulates Pillar Cell Development in the Organ of Corti," J. Neurosci. 22(21): 9368-77 (2002), which are hereby incorporated by reference in their entirety).

Suitable bone morphogenic protein antagonists include: AMN (amnionless homolog); BAMB1 (NMA); BMP1 (TLD); CER1 (Cerebrus); CHRD (chordin); CHRDL1 (Neutralin-1); CHRDL1 (Chordin-like 2); CRIM1 (cystein-rich motor neuron-1); FLJ38607 Dante/Coco homolog; FST (follistatin); FLTL1 (follistatin-like 1); FLTL3 (follistatin-like 3); FLTL4 (follistatin-like 4); FLTL5 (follistatin-like 5); GREM1 (gremlin); GREM2 (PRDC orthologue); IGFBP7 (follistatin-like 2/MAC25); LOC286015 (like Kielin); NBL1 (DAN); NOG (noggin); SOST (sclerostin); TLL1 (tolloid-like 1); TLL2 (tolloid-like 2); TMEFF1 (transmembrane protein with EGF-like and two follistatin-like domains); TMEFF2 (transmembrane protein with EGF-like and two follistatin-like domains 2); and TWSG1 (twisted gastrulation).

Suitable platelet-derived growth factor receptor (PDGFR) inhibitors include STI571 or CGP 57148B (4-[(4-methyl-1-piperazinyl)methyl]-N-[4-methyl-3-[[4-(3-pyridinyl)o-2-yrimidinyl]amino]-pheny]benzamide methanesulfonate) (Kilic, et. al., "Intracranial Inhibition of Platelet-derived Growth Factor-Mediated Glioblastoma Cell Growth by an Orally Active Kinase Inhibitor of the 2-Phenylaminopyrimidine Class," *Cancer Res.* 60: 5143-50 (2000) and Uhrboom, et. al., "Dependence of Autocrine Growth Factor Stimulation in Platelet-Derived Growth Factor-B-Induced Mouse Brain Tumor Cells," *Int. J. Cancer* 85: 398-406 (2000), which are hereby incorporated by reference in their entirety) and the following compounds from the Calbiochem Catalog, which is hereby incorporated by reference in its entirety:

| Cat. No. | Product Name |
| --- | --- |
| 521230 | PDGF Receptor Tyrosine Kinase Inhibitor I |
| 521231 | PDGF Receptor Tyrosine Kinase Inhibitor II |
| 521232 | PDGF Receptor Tyrosine Kinase Inhibitor III |

RTP-zeta (also referred to herein as RTP-β or RTP β/ζ) inhibitors include the following compounds from Calbiochem Catalog, which is hereby incorporated by reference in its entirety:

| Cat. No. | Product Name |
| --- | --- |
| 203701 | bpV(HOpic) |
| 203695 | bpV(phen) |
| 203705 | bpV(pic) |
| 217691 | CDC25 Phosphatase Inhibitor BN82002 |
| 322130 | DMHV |
| 263200 | Dephostatin |
| 263202 | 3,4-Dephostatin |
| 263203 | 3,4-Dephostatin, Ethyl |
| 521000 | Phenylarsine Oxide |
| 540215 | Protein Tyrosine Phosphatase CD45 Inhibitor |
| 540200 | Protein Tyrosine Phosphatase Inhibitor I |
| 540205 | Protein Tyrosine Phosphatase Inhibitor II |
| 540210 | Protein Tyrosine Phosphatase Inhibitor III |
| 540211 | Protein Tyrosine Phosphatase Inhibitor IV |
| 557322 | RK-682, *Streptomyces* sp. |
| 567565 | Sodium Stibogluconate |
| 203694 | bpV(bipy) |

These molecules can modulate oligodendrocyte progenitor mobilization, division, proliferation, differentiation, and/or self-maintenance. In addition, they can modulate oligodendrocyte maturation, differentiation, myelin production, and/or axonal myelination.

Preferably, the neural progenitor cells are oligodendrocyte progenitor cells. These cells can be derived from a post-natal human, fetal, or an adult human.

Administration can be carried out in vivo or in vitro.

Another aspect of the present invention relates to a method of treating a subject for a condition modulated by underproduction, dysfunction, or loss of oligodendrocytes from post-natal or adult human white matter. This method involves administering to the subject an agonist or antagonist of one or more molecules set forth in Tables 1 and/or 2 under conditions effective to treat the condition modulated by underproduction, dysfunction, or loss of oligodendrocytes.

This embodiment can be carried out with the same agonists and antagonists of the same molecules described above.

Conditions modulated by underproduction, dysfunction, or loss of oligodendrocytes from post-natal or adult human white matter include the pediatric leukodystrophies, the lysomal storage diseases, congenital dysmyelination, cerebral palsy, inflammatory demyelination (e.g., multiple sclerosis), post-infectious and post-vaccinial leukoencephalitis, radiation- or chemotherapy-induced white matter damage, and vascular demyelination (e.g., stroke, trauma, hypertensive and diabetic leukoencephalopathy, spinal cord stroke and trauma, and spinal cord compression).

The compounds of the present invention can be administered orally, parenterally, for example, subcutaneously, intravenously, intramuscularly, intraperitoneally, by intranasal instillation, or by application to mucous membranes, such as, that of the nose, throat, and bronchial tubes. They may be administered alone or with suitable pharmaceutical carriers, and can be in solid or liquid form such as, tablets, capsules, powders, solutions, suspensions, or emulsions.

The active compounds of the present invention may be orally administered, for example, with an inert diluent, or with an assimilable edible carrier, or they may be enclosed in hard or soft shell capsules, or they may be compressed into tablets, or they may be incorporated directly with the food of the diet. For oral therapeutic administration, these active compounds may be incorporated with excipients and used in the form of tablets, capsules, elixirs, suspensions, syrups, and the like. Such compositions and preparations should contain at least 0.1% of active compound. The percentage of the compound in these compositions may, of course, be varied and may conveniently be between about 2% to about 60% of the weight of the unit. The amount of active compound in such therapeutically useful compositions is such that a suitable dosage will be obtained. Preferred compositions according to the present invention are prepared so that an oral dosage unit contains between about 1 and 250 mg of active compound.

The tablets, capsules, and the like may also contain a binder such as gum tragacanth, acacia, corn starch, or gelatin; excipients such as dicalcium phosphate; a disintegrating agent such as corn starch, potato starch, alginic acid;

a lubricant such as magnesium stearate; and a sweetening agent such as sucrose, lactose, or saccharin. When the dosage unit form is a capsule, it may contain, in addition to materials of the above type, a liquid carrier, such as a fatty oil.

Various other materials may be present as coatings or to modify the physical form of the dosage unit. For instance, tablets may be coated with shellac, sugar, or both. A syrup may contain, in addition to active ingredient, sucrose as a sweetening agent, methyl and propylparabens as preservatives, a dye, and flavoring such as cherry or orange flavor.

These active compounds may also be administered parenterally. Solutions or suspensions of these active compounds can be prepared in water suitably mixed with a surfactant, such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

The compounds of the present invention may also be administered directly to the airways in the form of an aerosol. For use as aerosols, the compounds of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

Figure 3:
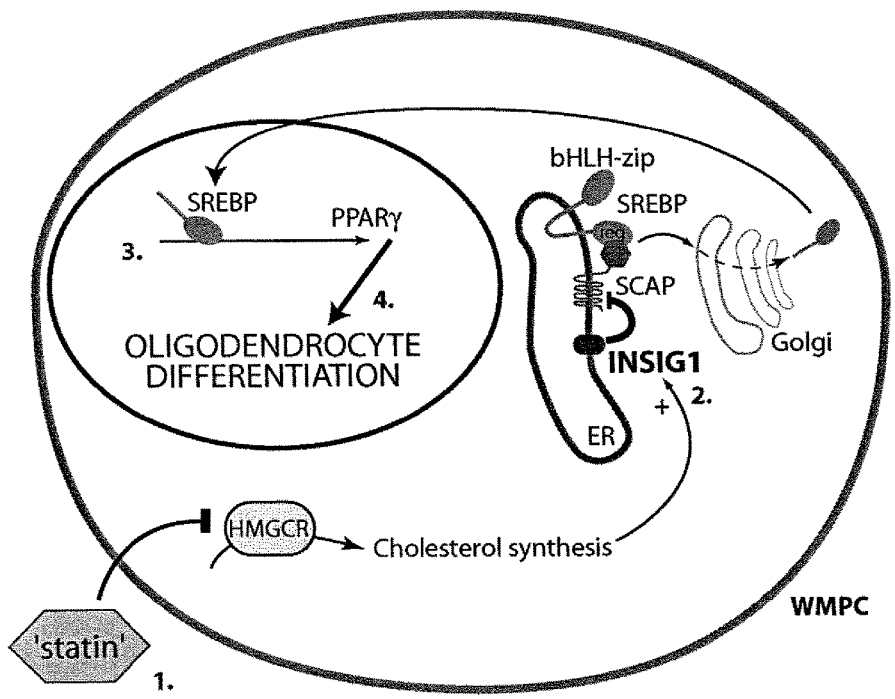
FIG. 3 shows the role of sterol synthesis enzymes and products in the differentiation of adult human oligodendrocyte progenitor cells. The identification of this gene expression pattern in adult human oligodendrocyte progenitor cells indicates that inhibition of sterol synthesis in these cells may lead to oligodendrocyte differentiation.

Another aspect of the present invention relates to a method differentiating oligodendrocyte progenitor cells to oligodendrocytes. This involves administering an inhibitor of sterol synthesis under conditions effective to differentiate oligodendrocyte progenitor cells to oligodendrocytes. Examples of suitable inhibitors of sterol synthesis include lovastatin, simvastatin, atorvastatin, pravastatin, fluvastatin, cerivastatin, and rosuvastatin. The compounds can be formulated and administered in substantially the manner described above. See also FIG. 3.

EXAMPLES

Example 1—Adult Human Subcortical White Matter

Adult human subcortical white matter was obtained from temporal lobe tissue removed from 48 patients at craniotomy, principally for medication-refractory epilepsy (age 17-56 years; 5 males and 3 female). Samples were obtained from patients who consented to tissue use under protocols approved by the New York Hospital-Cornell, Columbia Presbyterian Hospital, and University of Rochester-Strong Memorial Hospital Institutional Review Boards. The tissues were prepared and white matter progenitor cells freshly isolated as previously described (Nunes et al., "Identification and Isolation of Multipotential Neural Progenitor Cells from the Subcortical White Matter of the Adult Human Brain." *Nat Med* 9: 439-447 (2003), which is hereby incorporated by reference in its entirety). Briefly, samples were minced into PIPES solution (in mM: 120 NaCl, 5 KCl, 25 glucose, and 20 PIPES), then digested in papain-PIPES (11.4 U/ml papain; Worthington, Freehold, N.J.) and DNase I (10 U/ml; Sigma, St. Louis, Mo.), on a shaker for 1.5 hr at 37° C. The cells were collected by centrifugation at 200×g in an IEC Centra-4B centrifuge, resuspended in DMEM/F-12/N1 with DNase I (10 U/ml), and incubated for 30 min at 37° C. The samples were again spun, and their pellets recovered in 2 ml of DMEM/F-12/N1. They were then dissociated by sequentially triturating for 20, 10, and 5 times, respectively, through three glass Pasteur pipettes fire polished to decreasing bore diameters. The cells were passed through a 40 µm mesh into DMEM/F-12/N1, with 10% plasma-derived fetal bovine serum (PD-FBS; Cocalico Biologicals, Reamstown, Pa.) to stop the enzymatic dissociation. The cells were then suspended in DMEM/F12/N1 and incubated in A2B5-antibody containing supernatant (clone 105; American Type Culture Collection, Manassas, Va.) for 30-45 min at 4° C. on a shaker. The cells were washed 3× with PBS containing 0.5% bovine serum albumin and 2 mM EDTA, then incubated with 1:4 diluted microbead-tagged rat anti-mouse IgM antibody (MACS, Miltenyi Biotech) for 30 min at 4° C. on a shaker. The A2B5$^+$ cells were washed, resuspended, and separated using positive selection columns, type MS+/RS+ or LS+/VS+(MACS, Miltenyi Biotech). The total number of viable cells was determined using calcein (Molecular Probes).

Example 2—Affymetrix GeneChip Protocol

Immediately after sorting, RNA was extracted with Trizol (Invitrogen) and then purified using RNeasy (Qiagen), both according to manufacturer's specifications. 100 ng of total RNA was amplified using Affymatrix's small sample protocol (GeneChip® Eukaryotic Small Sample Target Labeling Technical Note), and 15 µg of cRNA was used on each U95Av2 GeneChip.

Example 3—Analysis of GeneChip Expression Data

Image files were processed using MAS5.0 to produce CHP files. Images were masked to remove streaks or smears present, and no scaling of data was performed during analysis. Data was then imported into GeneSpring (5.0, Silicon Genetics) and per chip normalization performed (using the 50th percentile of all measurements in that sample). Calculation of gene expression ratios was then performed by comparing the expression pattern of each A2B5-sorted sample to that of the unsorted population from which it had been extracted. This comparison effectively normalized sample-to-sample variation. The arithmetic mean ratio of A2B5-sorted to unsorted was then calculated from three separate patients. An estimate of error was generated using the Rocke-Lorenzato global error model, which takes into account the variability in the expression level of individual genes, compared to that of the entire data set. As a result, lower and more variably expressed genes are given larger error values, and are thus less likely to be deemed significant using statistical criteria.

Example 4—Statistical Assignment of Differential Expression

Transcripts deemed significantly enriched or depleted in the sorted cell pool fulfilled the criterion that their sorted:unsorted expression ratios differed significantly from 1; this was effectively a paired t-test of expression ratios. A Benjamin and Hochberg False Discovery Rate (FDR) of 20% was selected empirically; at that level, it was validated that 15 of 18 nominally-enriched genes subjected to qPCR validation were indeed enriched, while the other 3 were undetectable in the RNA obtained from unsorted cells, thus precluding ratio determination.

Example 5—Annotation of Probe Sets

Qualifying probe sets for each gene on the Affymetrix Human U95Av2 chip were identified using annotations available from NetAffx and Ensembl. Probe sets with conflicting annotations were verified by BLAST analysis of probe target sequence to the human genome. This process excluded mis-annotated probe sets. Annotation and further data analysis was then performed within an in-house Microsoft Access database.

Example 6—Real-Time PCR

The chosen genes validated by quantitative RT-PCR were designed to efficiently test the model generated based on array data alone (See FIG. 1). Primers and probes were either designed using Primer express (Applied Biosystems) or obtained as Assays-on-Demand directly from Applied Biosystems. For each sample, four separate reverse transcription reactions of 25 ng total RNA were performed as per manufacturer's protocol and the resulting cDNA diluted to 100 pg/µl. Four separate real-time PCR reactions with 500 pg/reaction, in addition 2 no-RT control reactions were performed to check for RNA-independent product amplification. For taqman real-time PCR, a 900 nM concentration of forward and reverse primers, and 250 nM FAM-labeled MGB probes. For SYBR Green real-time PCR, 300 nM forward and reverse primers were used. Human 18S RNA was used as an endogenous control, as described by the manufacturer (ABI). The relative abundance of transcript expression was calculated following normalization of the $C_t$ value to the matched unsorted white matter dissociate control, and the final expression ratio then normalized to the endogenous control. The mean, standard error, and significance testing of the individual samples were calculated by first performing a log transformation on the ratio data. The values presented in the tables are the anti-log of these values. Significance was tested using two-way one-sample t-test against a null ratio of 1 (n=4).

Example 7—Tyrosine Phosphatase Inhibition

WMPCs were distributed onto 12-well plates coated with poly-L-ornithine and fibronectin at $5 \times 10^4$ cells/ml in DMEM/F12/N1 supplemented with 10 ng/ml bFGF (Sigma), 10 ng/ml PDGF-AA (Sigma), and 2 ng/ml NT3 (R&D Systems). Stock solutions of 1 µM bpV(phen) (potassium bisperoxo (1,10-phenanthroline) oxovanadate (V); Calbiochem) were prepared before each use. Cells were exposed to concentrations of 0, 1, 5, 10, and 25 ng/ml of bV (phen) immediately upon plating, and every 2 days thereafter for 7 day in vitro.

Example 8—Immunocytochemistry

Cultures were exposed continuously to 10 µg/ml BrdU beginning 24 hours before fixation. After 7 days in vitro, A2B5 and O4 were immunolabeled as previously described (Roy et al., "Identification, Isolation, and Promoter-defined Separation of Mitotic Oligodendrocyte Progenitor Cells from the Adult Human Subcortical White Matter," *J. Neurosci* 19:9986-95 (1999), which is hereby incorporated by reference in its entirety). For multiple antigen labeling, O4 and A2B5 were localized on live cells that were then fixed with 4% paraformaldehyde and immunostained for BrdU. O4 supernatant was used at a dilution of 1:100 and monoclonal antibody A2B5 supernatant (clone 105, American Type Culture Collection) was used in a 1:1 ratio with DMEM/F12/N, both for 40 minutes at 4° C. Rat anti-BrdU antibody (Harlan) was used at a dilution of 1:200. Fixed cultures were counterstained with DAPI (10 ng/ml; Molecular Probes). The number of A2B5 and O4 stained and unstained cells were counted in 10 randomly chosen fields at each dosage level, from individual replicate samples (n=4). Statistical significance was assessed by one-way repeated measures analysis of variance (ANOVA), followed by Tukey's multiple comparisons test (GraphPad Prism 3.0, p<0.05).

Example 9—Adult Human WMPCs Expressed Oligodendrocyte Progenitor Marker Genes

Adult human subcortical white matter progenitor cells (WMPCs) were enriched by magnetic-activated cell sorting (MACS) using the A2B5 marker as previously described (Roy et al., "Identification, Isolation, and Promoter-defined Separation of Mitotic Oligodendrocyte Progenitor Cells From the Adult Human Subcortical White Matter." *J Neurosci* 19: 9986-95 (1999); Nunes et al., "Identification and Isolation of Multipotential Neural Progenitor Cells from the Subcortical White Matter of the Adult Human Brain." *Nat Med* 9: 439-447 (2003), which are hereby incorporated by reference in their entirety). From four epileptic temporal lobe resections cases, between $5 \times 10^5$ and $1 \times 10^6$ A2B5$^+$ cells, that comprised roughly 3% of all viably dissociated white matter cells, were obtained. To identify those genes whose expression distinguishes the A2B5$^+$ WMPC population from the other glial subtypes present in normal human adult white matter, microarray analysis was performed on both RNA extracted from WMPCs immediately after sorting and RNA extracted from the specific unsorted dissociates from which the sorts were derived. Beginning with at least 100 ng of total RNA per isolate, two rounds of RNA amplification were performed prior to hybridization to Affymetrix HG-U95Av2 GeneChips using Affymetrix's small sample protocol. Following microarray-wide normalization, the expression of individual genes in each WMPC isolate was normalized against that of the unsorted white matter dissociate from which it was derived, and the mean expression ratio calculated from the individual samples.

To analyze the microarray data, the expression of several known marker genes differentially expressed by glial progenitor cells was first determined (Table 3).

TABLE 3

Marker Gene Expression Profile of A2B5+ WMPCs

| | Ratio of mRNA expression A2B5+ WMPCs:unsorted WM Affymetrix U95Av2 (n = 3) | |
|---|---|---|
| *Oligodendrocyte Progenitor* | | |
| CSPG4 (NG2) | 38004_at | 19.41 ± 2.62 |
| PDGFRA | 1731_at [1] | 11.18 ± 0.89 |
| SIAT8A (GD3 synthase) | 40678_at | 5.25 ± 0.89 |
| *Oligodendrocyte Lineage* | | |
| CNP (CNPase) | 612_s_at | 1.64 ± 0.21 |
| NKX2-2 | 33605_at | 1.53 ± 0.42 |
| OLIG2 | 40624_at | 1.71 ± 0.39 |
| PLP1 (PLP/DM20) | 41158_at | 1.21 ± 0.19 |
| QKI | 39759_at | 1.06 ± 0.29 |
| SOX10 | 36018_at | 1.19 ± 0.26 |
| *Myelinating Oligodendrocyte* | | |
| GALC | 33936_at | 1.07 ± 0.20 |
| MAG | 38558_at | 1.22 ± 0.24 |
| MAL | 38051_at | 0.81 ± 0.14 |
| MBP | 35817_at | 1.32 ± 0.23 |
| MOBP | 38499_s_at | 0.28 ± 0.15 |
| MOG | 37868_s_at | 0.52 ± 0.25 |
| *Astrocyte* | | |
| AQP4 | 40793_s_at | 1.37 ± 0.98 |
| AQP9 | 34435_at | 0.29 ± 0.19 |
| GFAP | 40185_at | 1.70 ± 0.33 |
| GLUL (glutamine synthase) | 40522_at | 0.86 ± 0.15 |
| S100B | 235_at | 1.00 ± 0.14 |
| TNC (Tenascin C) | 32818_at | 1.40 ± 1.14 |
| *Neuronal progenitor/stem cell* [2] | | |
| ASCL1 (MASH1) | 40544_g_at | 12.32 ± 1.72 |
| DCX (doublecortin) | 34382_at | 7.56 ± 2.91 |
| HES1 | 37393_at | 5.13 ± 1.27 |
| *Neural lineage* [2] | | |
| ELAVL3 (HuC) | 38512_r_at | 1.13 ± 0.19 |
| ELAVL4 (HuD) | 40380_at | 2.50 ± 0.54 |
| MAP2 | 35422_at | 0.92 ± 0.49 |
| | 1972_s_at | 4.17 ± 0.56 |
| NEF3 (neurofilament medium) | 32512_at | 1.33 ± 0.13 |
| TUBA3 (Tα1 tubulin) | 40567_at | 0.84 ± .016 |
| *Endothelial* [2] | | |
| CDH5 (VE-Cadherin) | 37196_at | 0.58 ± 0.20 |
| TEK (TIE2) | 1595_at | 0.82 ± 0.56 |
| *Microglial* | | |
| CD68 | 33390_at | 0.49 ± 0.12 |
| CD86 | 36270_at | 0.27 ± 0.40 |
| HLA-DRA | 37039_at | 0.22 ± 0.14 |
| HLA-DRB1 | 41723_s_at | 0.22 ± 0.12 |

Genes/probe sets in bold indicate significant enrichment in WMPCs over unsorted dissociated white matter cells.
[1] For genes with multiple Affymetrix probe sets, the probe set with the most significant ratio of expression is shown.
[2] SOX1, DLX2/5, NEFL (neurofilament light) and VWF (von Willebrands factor) are not detected in either A2B5+ WMPCs or unsorted WM cells but are detected in human fetal VZ tissue.

The marker used to isolate adult WMPCs, the monoclonal A2B5 (Eisenbarth et al., "Monoclonal Antibody to a Plasma Membrane Antigen of Neurons," *Proc Natl Acad Sci USA* 76:4913-4917 (1979) and Roy et al., "Identification, Isolation, and Promoter-defined Separation of Mitotic Oligodendrocyte Progenitor Cells from the Adult Human Subcortical White Matter," *J Neurosci* 19:9986-95 (1999), which are hereby incorporated by reference in their entirety) recognizes $G_Q$ and $G_{T3}$ gangliosides and their O-acetylated derivatives (Farrer et al., "GT3 and its O-Acetylated Derivative are the Principal A2B5-Reactive Gangliosides in Cultured O2A Lineage Cells and are Down-Regulated Along with 0-Acetyl GD3 During Differentiation to Oligodendrocytes." *J Neurosci Res* 57: 371-380 (1999), which is hereby incorporated by reference in its entirety). It was found that the expression of GD3 synthase (SIAT8A), the enzyme that catalyzes the transfer of sialic acid from CMP-sialic acid to GM3 and by which GD3 and GT3 are generated was significantly enriched in the WMPC pool. This observation was confirmed with real-time RT-PCR analysis (qPCR) of GD3 synthase mRNA levels following normalization to 18S ribosomal RNA (one sample t-test, $H_0=1$, $p<0.01$; Table 4).

TABLE 4

Real Time RT-PCR Validation of Significantly Enriched Marker Gene

| | Ratio of mRNA expression A2B5+ WMPCs:unsorted WM qPCR (n = 3-4) |
|---|---|
| *Oligodendrocyte Progenitor* | |
| CSPG4 (NG2) | 15.05 (13.66-16.57; p < 0.001) [1] |
| PDGFRA | 22.67 (19.30-26.61; p < 0.001) |
| SIAT8A (GD3 synthase) | 9.39 (8.62-10.23; p < 0.01) |
| *Neuronal progenitor/stem cell* | |
| ASCL1 (MASH1) | 18.67 (15.97-21.82; p < 0.05) |
| HES1 | 12.52 (11.86-13.21; p < 0.001) |

[1] Ranges in parenthesis indicates plus/minus one standard deviation.

Furthermore, microarray analysis revealed strong expression of PDGFαR and NG2 (CSPG4), two canonical markers of oligodendrocyte progenitors in vivo which were confirmed by qPCR (Tables 3 and 4).

The oligodendrocyte progenitor lineage bHLH transcription factors olig2 and Nkx2.2 were also detected in the WMPC profile. However, neither gene was significantly enriched compared to the unsorted white matter presumably since mature oligodendrocytes also express olig2 and Nkx2.2 (Lu et al., "Sonic Hedgehog—Regulated Oligodendrocyte Lineage Genes Encoding bHLH Proteins in the Mammalian Central Nervous System," *Neuron* 25: 317-29 (2000); Watanabe et al., "Transient Upregulation of Nkx2.2 Expression in Oligodendrocyte Lineage Cells During Remyelination," *Glia* 46: 311-322 (2004), which are hereby incorporated by reference in their entirety). Similarly, more mature oligodendrocytic transcripts, including CNP and the myelin protein genes, myelin basic protein (MBP) and proteolipid protein (PLP1), were under-expressed by WMPCs relative to their parental white matter. Markers of other white matter phenotypes, namely astrocytes, microglia, and endothelial cells, were either unenriched or relatively depleted in WMPCs (Table 3). Thus, the transcriptional profile of A2B5-sorted WMPCs exhibited the differential expression of a number of genes previously associated with oligodendrocyte progenitor cells.

Interestingly, several markers of early neural cell growth and migration were noted to be differentially expressed by WMPCs. Doublecortin (DCX), which is expressed on migrating immature cells during development, was >8-fold enriched in WMPCs. GAP43, a growth and regeneration-associated marker of process extension, was significantly enriched >4-fold in WMPCs, confirming earlier reports of GAP43's expression by rodent oligodendrocyte progenitors (Curtis et al., "Down-regulation of GAP-43 During Oligodendrocyte Development and Lack of Expression by Astrocytes In Vivo: Implications for Macroglial Differentiation," *Eur J Neurosci* 3:876-886 (1991; Fanarraga et al., O-2A Progenitors of the Mouse Optic Nerve Exhibit a Developmental Pattern of Antigen Expression Different from the Rat," *Glia* 15:95-104 (1995), which are hereby incorporated by reference in their entirety). GAD67 mRNA, which encodes glutamate decarboxylase (GAD) and, as such serves as a marker of GABA production, was enriched >8 fold in A2B5-sorted WMPCs. Although GABA expression has previously not been described in oligodendrocyte lineage cells, GAD expression by these cells may have reflected their potential to generate GABAergic neurons when cultured in low density (Nunes et al., "Identification and Isolation of Multipotential Neural Progenitor Cells from the Subcortical White Matter of the Adult Human Brain," *Nat Med* 9:439-447 (2003), which is hereby incorporated by reference in its entirety).

Example 10—Adult WMPCs are Transcriptionally Distinct from the Local White Matter Environment The Affymetrix U95Av2 GeneChip analyzes the expression of approximately 8,500 genes. 53% and 56% of the represented genes were present in at least one sample of the A2B5-sorted WMPC and unsorted dissociate transcript pools, respectively. The degree of overlap was large; 92% of those genes expressed in the A2B5-sorted pool were detected in the unsorted dissociate. A set of genes whose expression was significantly enriched in the A2B5-sorted WMPC-enriched population compared to the unsorted white matter dissociate was next identified. Using Genespring (Silicon Genetics) to analyze to array data base, those probe sets that were deemed 'absent' in all three A2B5-sorted profiles were removed. The remainder comprising reproducibly hybridized oligonucleotides were used to generate a list of probe sets whose expression was significantly higher in sorted cells than unsorted dissociate. The resulting list of approximately 250 probe sets (<5% of total) was then pruned by removing those that were either ambiguously annotated as mapping to multiple genes or were novel (by virtue of not yet having been annotated to NCBI LocusLink identifiers). The remaining probe sets were annotated to 210 distinct genes (Table 1). For each identified gene, additional probe sets were then identified. Transcripts depleted from the A2B5-sorted WMPC-enriched population were determined by the same analysis procedure by inverting the expression ratios in the A2B5-sorted pool. The number of depleted transcripts was much smaller with only 51 probe sets identified that mapped to 51 distinct genes (Table 2).

The frequency of functionally related transcripts was next examined to determine relevant functional categories of genes. Over represented functional categories in the A2B5-sorted WMPC cell profile were determined by comparison with the entire population of genes on the HG-U95Av2 microarray. Using the EASE software tool (Hosack et al., "Identifying Biological Themes Within Lists of Genes with EASE," *Genome Biol* 4:R70 (2003), which is hereby incorporated by reference in its entirety) to examine the Gene Ontology (GO) biological process annotation of WMPC-enriched genes, it was found that genes belonging to the neurogenesis, cell adhesion, and cell communication categories were over-represented in the WMPC profile ($p<0.05$, EASE score/adjusted Fisher exact test with post-hoc comparisons; Table 5).

TABLE 5

EASE Over-Represented Gene Analysis of Significantly Enriched Genes in A2B5+ WMPC

| Gene ontology category | List Hits | Population Hits | EASE score | Bootstrap all probabilities |
|---|---|---|---|---|
| cell adhesion | 33 | 441 | 0.000 | 0.001 |
| cell-cell adhesion | 14 | 133 | 0.000 | 0.001 |
| neurogenesis | 22 | 307 | 0.000 | 0.001 |
| morphogenesis | 37 | 731 | 0.000 | 0.003 |
| cell communication | 83 | 2255 | 0.000 | 0.005 |
| organogenesis | 35 | 687 | 0.000 | 0.005 |
| cellular process | 138 | 4485 | 0.000 | 0.018 |
| homophilic cell adhesion | 8 | 56 | 0.000 | 0.021 |
| cell migration | 7 | 43 | 0.001 | 0.032 |
| synaptic transmission | 13 | 199 | 0.005 | 0.178 |
| development | 47 | 1258 | 0.005 | 0.198 |
| transmission of nerve impulse | 13 | 204 | 0.006 | 0.216 |
| potassium ion transport | 8 | 89 | 0.007 | 0.282 |
| metal ion transport | 12 | 202 | 0.013 | 0.451 |
| monovalent inorganic cation transport | 11 | 183 | 0.018 | 0.539 |
| sterol biosynthesis | 4 | 24 | 0.022 | 0.624 |
| lipid metabolism | 17 | 366 | 0.023 | 0.638 |
| ion transport | 17 | 370 | 0.025 | 0.675 |
| alcohol metabolism | 10 | 170 | 0.028 | 0.726 |
| sterol metabolism | 5 | 48 | 0.033 | 0.786 |
| transport | 41 | 1194 | 0.035 | 0.818 |
| circadian rhythm | 3 | 12 | 0.036 | 0.822 |
| cation transport | 13 | 268 | 0.039 | 0.838 |
| cell motility | 13 | 269 | 0.040 | 0.847 |
| glutamate signaling pathway | 3 | 13 | 0.041 | 0.857 |
| secretory pathway | 7 | 101 | 0.043 | 0.871 |
| cell growth | 6 | 76 | 0.043 | 0.871 |
| posttranslational membrane targeting | 3 | 15 | 0.054 | 0.926 |
| rhythmic behavior | 3 | 15 | 0.054 | 0.926 |
| central nervous system development | 6 | 83 | 0.059 | 0.948 |
| cell-cell signaling | 18 | 449 | 0.062 | 0.955 |
| organelle organization and biogenesis | 14 | 321 | 0.063 | 0.958 |
| microtubule-based process | 7 | 112 | 0.064 | 0.960 |
| heterophilic cell adhesion | 5 | 61 | 0.068 | 0.968 |
| cytoskeleton organization and biogenesis | 11 | 233 | 0.071 | 0.971 |
| muscle attachment | 2 | 3 | 0.074 | 0.974 |
| natural killer cell mediated cytolysis | 2 | 3 | 0.074 | 0.974 |
| cholesterol biosynthesis | 3 | 18 | 0.075 | 0.975 |
| cholesterol metabolism | 4 | 42 | 0.089 | 0.988 |
| germ-cell migration | 2 | 4 | 0.097 | 0.994 |
| glutamate transport | 2 | 4 | 0.097 | 0.994 |
| steroid metabolism | 6 | 97 | 0.099 | 0.995 |
| Total annotated with GO biological process | 204 | 8027 | | |

The list of significantly enriched probe sets in WMPCs was transferred to the EASE software algorithm (version 2). Over-represented gene ontology biological process categories were determined by comparison against the population of all Affymetrix probe sets on the U95Av2 array. Both EASE exact fisher scores and bootstrap probabilities, using 1000 iterations, were calculated. Significance cut-offs are illustrated as solid bars, at $p < 0.05$ bootstrap all possibilities (upper bar) and $p < 0.05$ EASE score (lower bar).
Interestingly, cell adhesion, neurogenesis and cell communication categories were significantly over-represented in the WMPC-specific genes.

It was also noted that genes involved in sterol and cholesterol biosynthesis were differentially expressed by the WMPC pool. In contrast, when the same analysis was performed on genes depleted from the WMPC pool, it was found that genes involved in immune and inflammatory responsiveness were selectively under-represented in sorted WMPCs (Table 6).

TABLE 6

EASE Over-Represented Gene Analysis of Significantly Depleted Genes in A2B5+ WMPC

| Gene ontology category | List Hits | Population Hits | EASE score | Bootstrap all probabilities |
|---|---|---|---|---|
| response to biotic stimulus | 17 | 685 | 0.000 | 0.001 |
| defense response | 16 | 631 | 0.000 | 0.001 |
| response to external stimulus | 18 | 971 | 0.000 | 0.001 |
| immune response | 13 | 573 | 0.000 | 0.002 |
| inflammatory response | 7 | 138 | 0.000 | 0.003 |
| innate immune response | 7 | 143 | 0.000 | 0.003 |
| response to chemical substance | 6 | 143 | 0.001 | 0.022 |
| response to pest/pathogen/parasite | 9 | 384 | 0.001 | 0.022 |
| response to wounding | 7 | 220 | 0.001 | 0.024 |
| chemotaxis | 5 | 92 | 0.002 | 0.025 |
| taxis | 5 | 92 | 0.002 | 0.025 |
| antigen processing, exogenous antigen via MHC class II | 3 | 12 | 0.002 | 0.029 |
| antigen presentation, exogenous antigen | 3 | 13 | 0.002 | 0.036 |
| signal transduction | 20 | 1773 | 0.003 | 0.038 |
| response to stress | 11 | 651 | 0.003 | 0.046 |
| antigen presentation | 3 | 21 | 0.006 | 0.094 |
| antigen processing | 3 | 21 | 0.006 | 0.094 |
| cytosolic calcium ion concentration elevation | 3 | 31 | 0.013 | 0.210 |
| cell communication | 21 | 2255 | 0.018 | 0.256 |
| response to abiotic stimulus | 6 | 349 | 0.048 | 0.589 |
| G-protein signaling, coupled to IP3 second messenger (phospholipase C activating) | 3 | 64 | 0.052 | 0.617 |
| humoral immune response | 4 | 148 | 0.052 | 0.620 |
| phosphatidylinositol-4\,5-bis-phosphate hydrolysis | 2 | 11 | 0.061 | 0.685 |
| humoral defense mechanism (sensu Invertebrata) | 3 | 87 | 0.088 | 0.831 |
| antimicrobial humoral response | 3 | 87 | 0.088 | 0.831 |
| antimicrobial humoral response (sensu Invertebrata) | 3 | 87 | 0.088 | 0.831 |
| circulation | 3 | 89 | 0.092 | 0.843 |
| Total annotated with GO biological process | 47 | 8027 | | |

The list of significantly depleted probe sets in WMPCs was transferred to the EASE software algorithm (version 2). Over-represented gene ontology biological process categories were determined by comparison against the population of all Affymetrix probe sets on the U95Av2 array. Both EASE exact fisher scores and bootstrap probabilities, using 1000 iterations, were calculated. Significance cut-offs are illustrated as solid bars, at $p < 0.05$ bootstrap all possibilities (upper bar) and $p < 0.05$ EASE score (lower bar). Several immune and inflammatory-related biological process categories were found to be depleted from WMPC-expressed genes.

Example 11—WMPCs Express a Cohort Receptor Suggesting Active Environmental Interrogation Belying their apparent relative quiescence, adult WMPCs were found to express a set of receptors that would permit their responsiveness to a wide variety of both protein growth factors and neurotransmitters. Several G protein coupled receptors were differentially expressed by adult human WMPCs, the most prominent of which was the cannabinoid receptor (CNR1) (Molina-Holgado et al., "Cannabinoids Promote Oligodendrocyte Progenitor Survival: Involvement of Cannabinoid Receptors and Phosphatidylinositol-3 kinase/Akt Signaling," *J Neurosci* 22: 9742-9753. (2002), which is hereby incorporated by reference in its entirety), which was confirmed to be >10-fold higher in the sorted than unsorted cells by qPCR ($p<0.01$). In addition, the relatively uncharacterized GPR19 (O'Dowd et al., "A Novel Gene Codes for a Putative G Protein-Coupled Receptor With an Abundant Expression in Brain," *FEBS Lett* 394: 325-329 (1996), which is hereby incorporated by reference in their entirety) was one of the more significantly differentially expressed transcripts in these cells.

Several tyrosine kinases and phosphatases were also differentially expressed (Tables 7 and 8).

TABLE 7

WMPC Enriched Genes - Tyrosine Kinase Receptors

| Tyrosine Kinase Receptors | | Ratio of mRNA expression A2B5+ WMPCs:unsorted WM Affymetrix U95Av2 (n = 3) |
|---|---|---|
| ErbB3 | 32787_at[1] | 1.60 ± 0.29 |
| FGFR1 | 2056_at | 2.09 ± 0.40 |
| FGFR3 | 31805_at | 10.21 ± 4.54 |
| IGF1R | 34718_at | 1.60 ± 1.68 |
| INSR (Insulin receptor) | 33162_at | 1.09 ± 0.18 |
| NTRK2 (TrkB) | 1355_g_at | 1.46 ± 0.26 |
| PDGFRA | 1731_at | 11.18 ± 0.89 |

Probe sets in bold indicate significant enrichment in WMPCs over unsorted dissociated white matter cells.

[1] For genes with multiple Affymetrix probe sets, the probe set with the most significant ratio of expression is shown.

TABLE 8

WMPC Enriched Genes - RTPβ/ζ and Related Molecules

| | | Ratio of mRNA expression A2B5+ WMPCs:unsorted WM | |
|---|---|---|---|
| | | Affymetrix U95Av2 (n = 3) | qPCR (n = 3-4) |
| PTPRZ1 (RTPβ/ζ) | 1364_at | 8.74 ± 0.30 | 15.62 (10.43-23.38; $p < 0.01$) |
| PTN (pleiotrophin) | 234_s_at[1] | 4.18 ± 0.37 | 4.42 (3.72-5.25; $p < 0.01$) |
| SDC3 (syndecan-3) | 32092_at | 2.69 ± 0.34 | 7.22 (5.92-8.81; $p < 0.01$) |
| CASK | 31854_at | 2.20 ± 0.23 | 4.66 (4.15-5.22; $p < 0.001$) |

[1] For genes with multiple Affymetrix probe sets, the probe set with the most significantly enriched ratio of expression is shown.

Among kinases, both PDGFαR and FGFR3, the nominal high-affinity receptor for FGF4 and FGF9, were expressed 10-fold higher by sorted WMPCs compared to the surrounding white matter. A number of other tyrosine kinases, including FGFR1, ErbB3, insulin receptor (INSR), IGF-1 receptor (IGF1R), and TrkB (NTRK2), were expressed by WMPCs, though no more so than by their surrounding white matter. Among receptor tyrosine phosphatases, RTPβ/ζ was highly expressed and differentially so, as were most of its known ligands (see below). A relatively uncharacterized adenyl cyclase, adenylate cyclase 8 (ADCY8), was identified as highly differentially expressed, being over 17 fold higher in A2B5-sorted WMPCs.

WMPCs also expressed differentially high levels of surface receptors for several neurotransmitters, including both ionotropic and metabotropic receptors for GABA, glutamate and glycine (Table 1). This suggests a high degree of responsiveness to the local transmitter environment and suggests greater activity-dependent responsiveness than might have been expected from a nominally quiescent phenotype. In general terms, though the normative roles of all of these receptors in modulating adult WMPCs is unclear, their identification presents a set of clear targets for pharmacological intervention.

Example 12—WMPCs Expressed Both Receptor Tyrosine Phosphatase β/ζ and its Ligand, Pleiotrophin Receptor tyrosine phosphatase zeta (RTPβ/ζ) was the single most significantly enriched receptor-encoding gene in this analysis, and was >15 fold enriched in WMPCs relative to unsorted cells by qPCR (Table 8; $p<0.01$). The Affymetrix probe set and qPCR primers were specific for the intracellular phosphatase domain of RTPβ/ζ, as opposed to its secreted ectodomain, phosphacan. To distinguish between the short and long receptor isoforms of RTPβ/ζ, specific qPCR primers were designed for each. Although both receptor isoforms were significantly more expressed in the WMPC, the longer isoform containing the glycosaminoglycan side chains was >25 fold enriched in WMPCs ($p<0.001$).

Importantly, the only known soluble ligand of RTPβ/ζ, pleiotrophin (PTN) (Meng et al., "Pleiotrophin Signals Increased Tyrosine Phosphorylation of Beta Beta-Catenin Through Inactivation of the Intrinsic Catalytic Activity of the Receptor-Type Protein Tyrosine Phosphatase Beta/Zeta," *Proc Natl Acad Sci USA* 97: 2603-2608 (2000), which is hereby incorporated by reference in its entirety) was also found to be expressed significantly higher in the WMPC-enriched profile by both microarray and qPCR analysis ($p<0.01$). Besides binding RTPβ/ζ, PTN has also been shown to bind the syndecan family of transmembrane heparin-sulphate proteoglycans. Interestingly then, syndecan-3 (SDC3) mRNA was also differentially expressed by sorted adult human WMPCs, as has been reported in rat oligodendrocyte progenitors (Bansal et al., "Regulation of FGF Receptors in the Oligodendrocyte Lineage," *Mol Cell Neurosci* 7: 263-275 (1996); Winkler et al., "Syndecan-3 and Perlecan Are Differentially Expressed by Progenitors and Mature Oligodendrocytes and Accumulate in the Extracellular Matrix," *J Neurosci Res* 69: 477-487 (2002), which are hereby incorporated by reference in their entirety).

Example 13—Inhibition of Tyrosine Phosphatase Activity Induces Oligodendrocyte Differentiation in WMPCs Due to the high expression of the tyrosine phosphatase receptor RTPβ/ζ in WMPCs, the effect of tyrosine phosphatase inhibition on the differentiation of WMPCs was assessed. bpV(phen), a known potent inhibitor of tyrosine phosphatase activity, was used to induce inhibition (Posner et al., "Peroxovanadium Compounds. A New Class of Potent Phosphotyrosine Phosphatase Inhibitors Which Are Insulin Mimetics," *J Biol Chem* 269: 4596-4604 (1994); Bevan et al., "Selective Activation of the Rat Hepatic Endosomal Insulin Receptor Kinase. Role for the Endosome in Insulin Signaling," *J Biol Chem* 270: 10784-10791 (1995); Faure et al., "Arrest at The G2/M Transition of the Cell Cycle by Protein-Tyrosine Phosphatase Inhibition: Studies on a Neuronal and a Glial Cell Line," *J Cell Biochem* 59: 389-401 (1995), which are hereby incorporated by reference in their entirety). Cultures maintained for 7 days exhibited a significant decline in progenitor A2B5+ cells (15±2.2% to 4±0.5%) with the addition of 25 ng/ml of bpV(phen)(n=4 patients) (FIGS. 1A-B and E). Conversely, the percentage of O4+ cells increased dramatically (20±8.4% to 54±17.6%) when treated 25 ng/ml of bpV(phen) (n=4 patients) (FIG. 1C-E). Statistical significance was first detected at 1 ng/ml bpV(phen) in the A2B5 positive population and 10 ng/ml bpV(phen) in the O4 positive population. The O4/A2B5 ratio rose drastically from under 10 percent to 70 percent in response to 25 ng/ml treatment with bpV(phen) (FIG. 1E). Total cell number remained unchanged between dosage levels as did the number of A2B5+ BrdU+ cells, suggesting the observed effect was due to induction of oligodendrocyte differentiation.

Example 14—WMPCs Express Surface Adhesion Molecules that May Interact with RTPβ/ζ

The coincident differential expression by WMPCs of both pleiotrophin and its two known receptors, RTPβ/ζ and syndecan, and the importance of both RTPβ/ζ and syndecan-dependent signaling in transcriptional modulation, suggested the wisdom of further investigating both RTPβ/ζ and syndecan binding partners in these cells. To this end, it was first examined whether WMPCs were enriched in syndecan-3 binding partners that might suggest its importance beyond that of a PTN sequestration moiety. Previous studies have shown that syndecan is subject to regulated intramembrane proteolysis, that leads to the release of the PDZ-containing cytosolic protein CASK from syndecan's cytoplasmic domain (Schulz et al., "Syndecan 3 Intramembrane Proteolysis is Presenilin/Gamma-Secretase-Dependent and Modulates Cytosolic Signaling," *J Biol Chem.* (2003), which is hereby incorporated by reference in its entirety). Importantly, CASK acts as a transcriptional regulator when not bound to syndecan; once released by syndecan, it translocates to the nucleus, where it binds to and activates the T-box family transcription factor, TBR1, inducing transcription of T-box target genes (Hsueh et al., "Nuclear Translocation and Transcription Regulation by the Membrane-Associated Guanylate Kinase CASK/LIN-2," *Nature* 404: 298-302 (2000), which is hereby incorporated by reference in its entirety). It was found that CASK was indeed significantly enriched in WMPCs in both the microarray and qPCR analyses (Table 8), suggesting the competence of this regulatory pathway in adult WMPCs.

It was next examined if WMPCs were enriched in RTPβ/ζ's binding partners. Although pleiotrophin is the only known soluble ligand for RTPβ/ζ, among other RTPβ/ζ binding partners, the extracellular matrix glycoprotein tenascin-R (TNR) (Milev et al., "High Affinity Binding and Overlapping Localization of Neurocan and Phosphacan/Protein-Tyrosine Phosphatase-Zeta/Beta With Tenascin-R, Amphoterin, and The Heparin-Binding Growth-Associated Molecule," *J Biol Chem* 273: 6998-7005 (1998), which is hereby incorporated by reference in its entirety), and CAM family members NrCAM (Sakurai et al., "Induction of Neurite Outgrowth Through Contactin and Nr-CAM by Extracellular Regions of Glial Receptor Tyrosine Phosphatase Beta." *J Cell Biol* 136: 907-918 (1997), which is hereby incorporated by reference in its entirety) and NCAM1 (Milev et al., "Interactions of the Chondroitin Sulfate Proteoglycan Phosphacan, the Extracellular Domain of a Receptor-Type Protein Tyrosine Phosphatase, With Neurons, Glia, and Neural Cell Adhesion Molecules," *J Cell Biol* 127: 1703-1715 (1994), which is hereby incorporated by reference in its entirety) were also differentially expressed by isolated WMPCs (Table 9).

TABLE 9

WMPC Enriched Genes - CAMs and ECM Molecules

| | | Ratio of mRNA expression A2B5+ WMPCs:unsorted WM Affymetrix U95Av2 (n = 3) |
|---|---|---|
| Cadherins | | |
| CDH11 (OB-cadherin) | 36976_at | 2.14 ± 0.31 |
| CDH13 (T-cadherin) | 482_at | 2.40 ± 0.40 |
| CDH18 (EY-cadherin) | 173_at | 3.03 ± 0.63 |
| PCDH8 (Arcadlin) | 32368_at | 4.79 ± 1.10 |
| KIAA1775 (MT-protocadherin) | 37857_at | 1.96 ± 0.17 |
| Ig-CAMs | | |
| NCAM1 | 41289_at | 2.51 ± 0.16 |
| DSCAM | 36699_at | 6.94 ± 0.71 |
| OBCAM | 41093_at | 13.87 ± 3.28 |
| CHL1 | 34193_at | 11.80 ± 3.96 |
| NRCAM | 37286_at[1] | 13.62 ± 2.77 |
| Chondroitin Sulphate Proteoglycans | | |
| CSPG2 (versican) | 38111_at | 8.36 ± 0.69 |
| CSPG3 (brevican) | 32642_at | 5.66 ± 0.43 |
| CSPG4 (NG2) | 38004_at | 19.41 ± 2.62 |
| CSPG5 (neuroglycan C) | 39966_at | 6.88 ± 1.18 |
| Other ECM molecules | | |
| TNR (Tenascin-R) | 41016_at | 14.66 ± 0.75 |

[1]For genes with multiple Affymetrix probe sets, the probe set with the most significant ratio of expression is shown.

Indeed, virtually every described heterophilic ligand of RTPβ/ζ was represented, highlighting the likely importance of in cis recognition of RTPβ/ζ and RTPβ/ζ-dependent signaling to the maintenance of WMPCs. Since RTPβ/ζ is able to mediate the dephosphorylation of β-catenin, which permits catenin translocation to the nucleus and consequent catenin-dependent transcriptional activation (Meng et al., "Pleiotrophin Signals Increased Tyrosine Phosphorylation of Beta Beta-Catenin Through Inactivation of the Intrinsic Catalytic Activity of the Receptor-Type Protein Tyrosine Phosphatase Beta/Zeta," *Proc Natl Acad Sci USA* 97: 2603-2608 (2000), which is hereby incorporated by reference in its entirety), it would seem likely that the functions of RTPβ/ζ's binding partners may be to regulate RTPβ/ζ-dependent modulation of β-catenin's basal phosphorylation state in these cells.

Example 15—Cell-Cell Adhesion and Extracellular Matrix Molecules of Adult Human WMPCs Over 20 known and putative cell adhesion molecules were enriched in the WMPC mRNA pool. These included members of the cadherin, CAM, chondroitin sulfate proteoglycan (CSPG), and tenascin gene families (Table 9). Three classical cadherins and two protocadherins were significantly enriched in the WMPC pool. Two type II cadherins, cadherin (CDH) 11 and 18, that mediate homotypic Ca-dependent cell adhesion, had previously been shown to be expressed in the brain, but their cell-type specificity had been unclear (Kimura et al., "Expression of Cadherin-11 Delineates Boundaries, Neuromeres, and Nuclei in the Developing Mouse Brain," *Dev Dyn* 206: 455-462 (1996), which is hereby incorporated by reference in its entirety). CDH11 can be induced by WNT activation of β-catenin, while CDH18 was initially identified as a β-catenin interacting protein (Shibata et al., "Identification of Human Cadherin-14, a Novel Neurally Specific Type II Cadherin, by Protein Interaction Cloning," *J Biol Chem* 272: 5236-5240 (1997); Hadeball et al., "*Xenopus* Cadherin-11 (Xcadherin-11) Expression Requires the Wg/Wnt Signal," *Mech Dev* 72: 101-113 (1998), which are hereby incorporated by reference in their entirety). In addition, two protocadherins, PCDH8 (Arcadlin) and KIAA1775 (MT-protocadherin) (Strehl et al., "Characterization of Two Novel Protocadherins (PCDH8 and PCDH9) Localized on Human Chromosome 13 and Mouse Chromosome 14," *Genomics* 53: 81-89 (1998); Nakajima et al., "Identification of Three Novel Non-Classical Cadherin Genes Through Comprehensive Analysis of Large cDNAs," *Brain Res Mol Brain Res* 94: 85-95 (2001), which are hereby incorporated by reference in their entirety), were also selectively enriched in WMPCs. Interestingly, WMPCs also differentially expressed the GPI-linked cadherin, CDH13, which is down-regulated in many tumor cells and acts as a negative regulator of EGF-stimulated neuroblastoma proliferation (Takeuchi et al., "Expression of T-Cadherin (CDH13, H-Cadherin) in Human Brain and Its Characteristics as a Negative Growth Regulator of Epidermal Growth Factor in Neuroblastoma Cells," *J Neurochem* 74: 1489-1497 (2000), which is hereby incorporated by reference in its entirety).

The neural cell adhesion molecule, NCAM1 mRNA, was significantly enriched in WMPCs, 2.5 fold (Table 9), in accord with the expression of its embryonic form by rat oligodendrocyte progenitors (Grinspan et al., "Platelet-Derived Growth Factor is a Survival Factor For PSA-NCAM+ Oligodendrocyte Pre-Progenitor Cells," *J Neurosci Res* 41: 540-551 (1995); Ben-Hur, et al., "Growth and Fate of PSA-NCAM+ Precursors of the Postnatal Brain," *J Neurosci* 18: 5777-5788 (1998), which are hereby incorporated by reference in their entirety). Several other CAM family members were also differentially expressed by WMPCs. These included DSCAM, OBCAM, CHL1 and NrCAM. DSCAM (Down syndrome CAM) binds homophilically and has been shown to be expressed in the corpus callosum (Yamakawa et al., "DSCAM: A Novel Member of the Immunoglobulin Superfamily Maps in a Down Syndrome Region and is Involved in the Development of the Nervous System," *Hum Mol Genet* 7: 227-237 (1998); Agarwala et al., "Down Syndrome Cell Adhesion Molecule DSCAM Mediates Homophilic Intercellular Adhesion," *Brain Res Mol Brain Res* 79: 118-126 (2000); Schmucker et al., "*Drosophila* Dscam is An Axon Guidance Receptor Exhibiting Extraordinary Molecular Diversity," *Cell* 101: 671-684 (2000), which are hereby incorporated by reference in its entirety). OBCAM (opioid-binding CAM), has been shown to be differentially expressed by young oligodendroglia during early myelination (Hachisuka, et al., "Localization of Opioid-Binding Cell Adhesion Molecule (OBCAM) in Adult Rat Brain," *Brain Res* 842: 482-486 (1999); Hachisuka et al., "Developmental Expression of Opioid- Binding Cell Adhesion Molecule (OBCAM) in Rat Brain," *Brain Res Dev Brain Res* 122: 183-191 (2000), which are hereby incorporated by reference in their entirety). The L1-family member CHL1, has been shown to be expressed by A2B5+ rat oligodendrocyte progenitors in vitro (Hillenbrand et al., "The Close Homologue of the Neural Adhesion Molecule L1 (CHL1): Patterns of Expression and Promotion of Neurite Outgrowth by Heterophilic Interactions," *Eur J Neurosci* 11: 813-826 (1999), which is hereby incorporated by reference in their entirety). Although its function is unclear, previous studies have highlighted the role of L1-dependent calcium signaling in modulating the migration and survival of early neural progenitor cells. As noted, NrCAM may be of special interest here since it has been shown to act as a heterophilic ligand for the RTPβ/ζ ectodomain (Sakurai et al., "Induction of Neurite Outgrowth Through Contactin and Nr-CAM by Extracellular Regions of Glial Receptor Tyrosine Phosphatase Beta." *J Cell Biol* 136: 907-918 (1997), which is hereby incorporated by reference in its entirety).

Importantly, the extracellular matrix molecule tenascin-R (TNR) was the second most significantly enriched gene in the A2B5-sorted WMPC pool (Table 9). Tenascin-R has been shown to be expressed by rodent A2B5+ oligodendrocyte progenitor in vitro (Jung et al., "Astrocytes and Neurons Regulate the Expression of the Neural Recognition Molecule Janusin by Cultured Oligodendrocytes," *Glia* 9: 163-175 (1993), which is hereby incorporated by reference in its entirety) and may regulate their lineage progression (Pesheva et al., "Tenascin-R is An Intrinsic Autocrine Factor For Oligodendrocyte Differentiation and Promotes Cell Adhesion by a Sulfatide-Mediated Mechanism," *J Neurosci* 17: 4642-4651 (1997), which is hereby incorporated by reference in its entirety). Like NrCAM, tenascin-R also binds to the RTPβ/ζ ectodomain (Milev et al., "High Affinity Binding and Overlapping Localization of Neurocan and Phosphacan/Protein-Tyrosine Phosphatase-Zeta/Beta With Tenascin-R, Amphoterin, and the Heparin-Binding Growth-Associated Molecule," *J Biol Chem* 273: 6998-7005 (1998), which is hereby incorporated by reference in its entirety), and is necessary for the normal distribution of RTPβ/ζ in white matter (Weber et al., "Mice Deficient for Tenascin-R Display Alterations of the Extracellular Matrix and Decreased Axonal Conduction Velocities in the CNS," *J Neurosci* 19: 4245-4262 (1999), which is hereby incorporated by reference in its entirety). Besides the well-characterized RTPβ/ζ binding molecules, ☐ four chondroitin-sulfate proteoglycans (CSPG) were differentially expressed by human WMPCs. These included versican (CSPG2), neurocan (CSPG3), NG2 (CSPG4), and neuroglycan C (CSPG5); each was enriched by 5-20 fold in A2B5-sorted WMPCs (Table 9). In addition to NG2, rodent oligodendrocyte progenitors had previously been shown to express versican (Niederost et al., "Bovine CNS Myelin Contains Neurite Growth-Inhibitory Activity Associated With Chondroitin Sulfate Proteoglycans," *J Neurosci* 19: 8979-8989 (1999); Asher et al., "Versican is Upregulated in CNS Injury and is a Product of Oligodendrocyte Lineage Cells," *J Neurosci* 22: 2225-2236 (2002), which are hereby incorporated by reference in their entirety) and neurocan (Chen et al., "Inhibition of Axon Growth by Oligodendrocyte Precursor Cells," *Mol Cell Neurosci* 20: 125-139 (2002), which is hereby incorporated by reference in their entirety). Yet neuroglycan C, a relatively recently cloned member of the aggrecan family localized to the brain (Yasuda et al., "Cloning and Chromosomal Mapping of the Human Gene of Neuroglycan C (NGC), a Neural Transmembrane Chondroitin Sulfate Proteoglycan With an EGF Module," *Neurosci Res* 32: 313-322 (1998), which is hereby incorporated by reference in its entirety), had not previously been reported to be expressed by oligodendrocyte progenitors. Remarkably then, essentially all known brain CSPGs were differentially expressed by adult WMPCs, at many-fold higher levels than the white matter from which they were derived.

Example 16—WMPCs Differentially Expressed Notch-Regulated Transcripts

As noted, a number of genes characteristic of oligodendrocyte progenitors were found differentially enriched in the A2B5+ progenitor pool. In addition though, several transcripts previously associated with less committed and early neural phenotypes were also differentially expressed by these cells. Two transcription factors though restricted to neural progenitors and stem cells respectively, MASH1 (ASCL1) and HES1, were highly enriched in the WMPC pool (Table 3). MASH1 expression was 12-fold greater by microarray, and >18-fold by qPCR, in A2B5+ cells relative to the unsorted white matter from which they were extracted (Table 2). HES1 was 5 fold higher by microarray, and >12 fold higher by qPCR. Both MASH1 and HES1 are downstream components of a notch signaling pathway that has already been shown to regulate oligodendrocyte progenitor differentiation in the rat optic nerve (Wang et al., "Notch Receptor Activation Inhibits Oligodendrocyte Differentiation," *Neuron* 21: 63-75 (1998), which is hereby incorporated by reference in its entirety).

A number of other notch-signaling components were expressed in WMPCs. As the Affymetrix U95Av2 chip does not contain probe sets to NOTCH1, it was determined whether WMPCs expressed notch receptor by qPCR. NOTCH1 was significantly enriched in WMPCs, expressed 60% higher in WMPCs than the unsorted white matter dissociate ($p<0.05$, Table 10).

TABLE 10

WMPC Enriched Genes - Notch Signaling Pathway

| | Ratio of mRNA expression A2B5+ WMPCs:unsorted WM | | |
|---|---|---|---|
| | Affymetrix U95Av2 (n = 3) Notch signaling | | qPCR (n = 3-4) |
| JAG1 (Jagged 1) | 35414_s_at | 1.26 ± 0.20 | 2.76 (2.53-3.02; p < 0.01) |
| JAG2 (Jagged 2) | 32137_at | 0.91 ± 0.13 | |
| NOTCH1 | no probe sets available | | 1.59 (1.50-1.70; p < 0.05) |
| NOTCH4 | 39048_at | 0.73 ± 0.32 | |
| MSI1 (musashi 1)[1] | not detected in adult samples | | 10.09 (7.31-13.93; n = 2, ns) |
| NUMB | 37693_at | 0.59 ± 0.21 | |

TABLE 10-continued

WMPC Enriched Genes - Notch Signaling Pathway

| | Affymetrix U95Av2 (n = 3) | | qPCR (n = 3-4) |
|---|---|---|---|
| | Notch signaling | | |
| RBPSUH (RBP-J) | no probe sets available | | 1.00 (0.78-1.29; n = 3, ns) |
| FHL1 | 32542_at | 4.50 ± 0.65 | 10.81 (6.62-17.64; p < 0.05) |
| FHL1B (RBP-J binding) | | | 9.19 (6.51-12.99; p < 0.01) |
| HES1 | 37393_at | 5.13 ± 1.27 | 12.52 (11.86-13.21; p < 0.001) |
| MASH1 | 40544_g_at | 12.32 ± 1.72 | 18.67 (15.97-21.82; p < 0.05) |

Genes in bold indicate significant enrichment in WMPCs over unsorted dissociated white matter cells.
[1]MSI1 was not detected in two of the unsorted samples preventing calculation of an appropriate ratio and therefore reducing the sample number.

NOTCH2/3 were not detected in either the WMPC or the unsorted dissociate; NOTCH4, though present, was not enriched in the WMPCs. Although notch ligands were poorly represented on the microarray, jagged1 (JAG1) was detected in both WMPCs and the unsorted dissociate (Table 10). Surprisingly, qPCR analysis revealed that WMPCs express significantly more JAG1 than their surrounding white matter environment (p<0.01), suggesting the capacity for lateral inhibition of differentiation among contiguous WMPCs.

Notch signaling typically activates transcription through CBF/RBP-J, which in turn up-regulates HES1 expression. In this regard, it was noted that FHL1, a novel RBP-J binding protein, was also significantly enriched in sorted WMPCs. FHL1 is a novel four-and-a-half LIM domain containing protein whose splice variant FHL1B contains an RBP-J binding domain (Lee et al., "Characterization of a Brain-Specific Nuclear LIM Domain Protein (FHL1B) Which is an Alternatively Spliced Variant of FHL1," *Gene* 237: 253-263 (1999), which is hereby incorporated by reference in its entirety). In the microarrays, significant expression of FHL1 was found and by qPCR it was determined that the FHL1B splice variant was enriched >10-fold (p<0.05).

The expression of numb protein inhibits notch signaling. The RNA-binding protein, musashi, binds the 3' UTR of numb mRNA, resulting in the down-regulation of numb protein, thereby relieving numb mediated inhibition of notch (Imai et al., "The Neural RNA-Binding Protein Musashi1 Translationally Regulates Mammalian Numb Gene Expression by Interacting With its mRNA," *Mol Cell Biol* 21: 3888-3900 (2001), which is hereby incorporated by reference in its entirety). In WMPCs, although only low levels of NUMB mRNA were found, the level of musashi1 mRNA was much greater in the sorted WMPCs than in unsorted white matter cells (Table 10). Together, the differential expression of so many positive regulators of the notch signaling pathway suggests the tonic activation of this pathway in the progenitor cell pool of the adult human white matter.

Example 17—Components of Both Retinoid and BMP Signaling Pathways are Expressed by WMPCs Apart from notch signaling, evidence for activation of retinoic acid signaling and response in WMPCs was found. Retinaldehyde dehydrogenase 3 (ALDH1A3), an enzyme responsible for the synthesis of retinoic acid in the lateral ganglionic eminence (Li et al., "A Retinoic Acid Synthesizing Enzyme in Ventral Retina and Telencephalon of the Embryonic Mouse," *Mech Dev* 95: 283-289 (2000), which is hereby incorporated by reference in its entirety), was enriched in WMPCs (>2 fold). This was accompanied by the increased expression, by >6-fold, of a synthetic retinoid-induced gene, RARRES2 (Nagpal et al., "Tazarotene-Induced Gene 2 (TIG2), a Novel Retinoid-Responsive Gene in Skin," *J Invest Dermatol* 109: 91-95 (1997), which is hereby incorporated by reference in its entirety), suggesting the presence of active RA signaling within the WMPC pool (Table 11).

TABLE 11

WMPC Enriched Genes - Retinoid and BMP Pathways

| | | Ratio of mRNA expression A2B5+ WMPCs:unsorted WM Affymetrix U95Av2 (n = 3) |
|---|---|---|
| Retinoic acid signaling | | |
| ALDH1A3 (RALDH3) | 36686_at | 2.27 ± 0.37 |
| RARRES2 | 34407_at | 6.20 ± 1.08 |
| BMP signaling | | |
| BMP2 | 1113_at[1] | 2.95 ± 0.25 |
| BMP7 | 38515_at | 4.93 ± 1.18 |
| NMA (BAMBI) | 37678_at | 2.55 ± 0.39 |
| NRLN1 | 37630_at | 14.46 ± 5.63 |

[1]For genes with multiple Affymetrix probe sets, the probe set with the most significant ratio of expression is shown.

Both BMP-2 and -7 were significantly enriched in WMPCs, between 3-6 and 5 fold respectively (Table 11). Along with overexpression of specific BMP ligands, expression of NMA/BAMBI (BMP and activin membrane-bound inhibitor), a negative regulator of BMP signaling whose expression is induced in cells exposed to BMPs (Onichtchouk et al., "Silencing of TGF-Beta Signalling by the Pseudoreceptor BAMBI," *Nature* 401: 480-485 (1999); Grotewold et al., "Bambi is Coexpressed With Bmp-4 During Mouse Embryogenesis," *Mech Dev* 100: 327-330 (2001), which are hereby incorporated by reference in their entirety), was found. In addition, neuralin/ventropin (NRLN1), a selective antagonist of BMP4 (Sakuta et al., "Ventroptin: a BMP-4 Antagonist Expressed in a Double-Gradient Pattern in the Retina," *Science* 293: 111-115 (2001), which is hereby incorporated by reference in its entirety), was also noted to be highly expressed. This observation was confirmed by qPCR, by which NRLN1 was >20-fold higher in WMPCs (p<0.05). This pattern of expression suggests an autocrine support of WMPC maintenance by BMP2 and 7-dependent pathways, with a concurrent inhibition of alternative BMPs, and BMP4 in particular, by neuralin.

Example 18—FGFR3 and PDGFαR Tyrosine Kinases are Differentially Expressed by WMPCs FGF signals have long been known to influence proliferation and differentiation of oligodendrocyte progenitors (for review see (Bansal et al., "Regulation of Oligodendrocyte Differentiation by Fibroblast Growth Factors," *Adv Exp Med Biol* 429: 69-77 (1997), which is hereby incorporated by reference in its entirety). In adult WMPCs, it was found that FGFR3, though neither FGFR1 nor R2, was significantly enriched (Table 7). Indeed, the type 3 FGF receptor has previously been found to be expressed on O4+ rodent oligodendrocyte progenitors in vitro (Bansal et al., "Regulation of FGF Receptors in the Oligodendrocyte Lineage," *Mol Cell Neurosci* 7: 263-275 (1996), which is hereby incorporated by reference in its entirety). This may have significance regarding ligand control of oligodendroglial mitogenesis, since it would predict that FGFR3's cognate ligands, FGFs 1, 4 and 9, might be especially efficacious at directing FGFR-dependent oligodendrocytic induction and expansion.

In this respect, it was also noted that the expression of sprouty 2 (SPRY2), an inhibitor of FGFR2 signaling (Hacohen et al., "Sprouty Encodes a Novel Antagonist of FGF Signaling That Patterns Apical Branching of the *Drosophila* Airways," *Cell* 92: 253-263 (1998), which is hereby incorporated by reference in its entirety), was increased in WMPCs relative to the unsorted population (1.96±0.26). Previous studies have shown that SPRY2 mRNA can be induced in vitro following FGF-2 signaling and can act as both an PDGF and FGF antagonist (Sasaki et al, "Identification of a Dominant Negative Mutant of Sprouty That Potentiates Fibroblast Growth Factor—But Not Epidermal Growth Factor-Induced ERK Activation," *J Biol Chem* 276: 36804-36808 (2001), which is hereby incorporated by reference in its entirety). Together, these data suggest an active permissiveness to FGR3 signaling concomitant with a lack, and perhaps tonic inhibition through SPRY2, of FGFR2 signaling.

PDGFαR was the third most significantly enriched annotated gene in WMPCs (Table 3). PDGFαR is expressed by rodent oligodendrocyte progenitors and mediates the mitogenic effect of PDGF. In addition to full length PDGFαR transcripts, a PDGFαR splice variant that does not contain the extracellular ligand-binding domain (Mosselman et al., "Developmentally Regulated Expression of Two Novel Platelet-Derived Growth Factor Alpha-Receptor Transcripts in Human Teratocarcinoma Cells," *Cancer Res* 54: 220-225 (1994), which is hereby incorporated by reference in its entirety), was enriched in WMPCs (5.16±0.98).

Example 19—Sterol Biosynthesis and Metabolism

A large number of genes involved in sterol biosynthesis and metabolism were differentially enriched in adult WMPCs (Table 12).

TABLE 12

WMPC Enriched Genes - Cholesterol Metabolism

| | | Ratio of mRNA expression A2B5+ WMPCs:unsorted WM Affymetrix U95Av2 (n = 3) Cholesterol Metabolism |
|---|---|---|
| BASP1 | 32607_at[1] | 1.94 ± 0.20 |
| APOD | 36681_at | 5.26 ± 0.85 |
| INSIG1 | 35303_at | 2.11 ± 0.28 |
| HMGCR | 39328_at | 2.38 ± 0.29 |
| IDI1 | 36985_at | 2.19 ± 0.18 |
| SC4MOL | 33369_at | 2.90 ± 0.49 |
| LDLR | 32855_at | 3.21 ± 0.33 |
| LRP1 | 38775_at | 1.75 ± 0.19 |
| PPARG (PPARγ)[2] | 37104_1t | 0.17 ± 0.13 |

[1]For genes with multiple Affymetrix probe sets, the probe set with the most significant ratio of expression is shown.
[2]PPARγ was significantly down-regulated in WMPCs compared to the unsorted white matter dissociate.

These genes included 3-hydroxy-3-methylglutaryl-coenzyme A reductase (HMGCR), the rate-limiting enzyme in cholesterol biosynthesis, and the low density lipoprotein receptor (LDLR), which acts to increase the availability of intracellular cholesterol. Significantly increased expression of INSIG1, which encodes an intracellular regulator of cholesterol metabolism thought to maintain pre-adipocytes in an undifferentiated state by inhibiting SREBP (Yang et al., "Crucial Step in Cholesterol Homeostasis: Sterols Promote Binding of SCAP to INSIG-1, a Membrane Protein That Facilitates Retention of SREBPs in ER," *Cell* 110: 489-500 (2002); Li et al., "Insig-1 "Brakes" Lipogenesis in Adipocytes and Inhibits Differentiation of Preadipocytes," *Proc Natl Acad Sci USA* 100: 9476-9481 (2003), which are hereby incorporated by reference in their entirety), was also found. Thus, cholesterol synthetic pathways appear primed in oligodendrocyte progenitors, before their terminal differentiation. In contrast, the transcription factor, PPARγ, which can induce adipocyte and oligodendrocyte cell differentiation (Walczak et al., "PPARadigms and PPARadoxes: Expanding Roles for PPARgamma in the Control of Lipid Metabolism," *J Lipid Res* 43: 177-186 (2002), which is hereby incorporated by reference in its entirety) and is expressed by both mature adipocytes and oligodendrocytes alike (Roth et al., "PPAR Gamma Activators Induce Growth Arrest and Process Extension in B12 Oligodendrocyte-Like Cells and Terminal Differentiation of Cultured Oligodendrocytes," *J Neurosci Res* 72: 425-435 (2003), which is hereby incorporated by reference in its entirety), was >5-fold more abundant in the unsorted white matter than in WMPCs (Table 12). The relative scarcity of this transcript in the WMPC pool was in accord with the undifferentiated state of these cells, and suggested that PPARγ expression is a concomitant of oligodendrocytic induction from the WMPC pool.

In this study, differences in gene expression between adult human WMPCs and the white matter environment from which they derive were identified, for the purpose of defining those environmentally-responsive signaling pathways differentially operative in these cells. By comparing the expressed RNA profiles of adult human WMPCs to those of the parental white matter tissue from which each progenitor sample has been extracted, differentially expressed genes were identified in the progenitor pool that appeared to complement others selectively expressed by the tissue. By this means, several hitherto unpredicted ligand-receptor interactions and their in cis modifiers were identified. These data suggest: 1) the importance of the RTPβ/ζ-pleiotrophin system in WMPC self-maintenance and mobilization; 2) the potentially co-regulated action of syndecan-dependent CASK release in WMPC maintenance; and 3) the role of notch signaling, as reflected by the differential expression of NOTCH1, HES1, musashi, and FHL1B by sorted WMPCs, in maintaining their phenotype; 4) the role of the BMP inhibitors neuralin and BAMBI in buffering the cellular response to ambient BMPs; and 5) the likely import of FGFR3 and PDGFαR in priming these cells for differentiation. In the absence of FGFR3 and PDGFαR ligands in the ambient white matter, these patterns of baseline gene expression might be expected to largely support the self-maintenance of WMPCs, while suppressing their differentiation.

On the basis of these data, a genomics-based model was generated for the regulatory control of adult human WMPCs, schematized here in FIG. 2. Its major elements follow.

RTPβ/ζ and its Ligands are Abundantly and Selectively Expressed by WMPCs.

Receptor tyrosine phosphatase-β/ζ was the most significantly enriched WMPC receptor gene in this analysis. Although RTPβ/ζ is expressed developmentally by radial cells and neural progenitors of the fetal ventricular zone (Canoll et al., "The Expression of a Novel Receptor-Type Tyrosine Phosphatase Suggests a Role in Morphogenesis and Plasticity of the Nervous System," *Brain Res Dev Brain Res* 75: 293-298 (1993), which is hereby incorporated by reference in its entirety), it has also been reported to be expressed in rat oligodendrocyte progenitors (Canoll et al., "Three Forms of RPTP-Beta are Differentially Expressed During Gliogenesis in the Developing Rat Brain and During Glial Cell Differentiation in Culture," *J Neurosci Res* 44: 199-215 (1996), which is hereby incorporated by reference in its entirety). Moreover, RTPβ/ζ knock-out mice exhibit impaired recovery from experimental allergic encephalitis (EAE) (Harroch et al., "A Critical Role For the Protein Tyrosine Phosphatase Receptor Type Z in Functional Recovery From Demyelinating Lesions," *Nat Genet* 32: 411-414 (2002), which is hereby incorporated by reference in its entirety). RTPβ/ζ acts to maintain the dephosphorylated state of β-catenin, so that RTPβ/ζ deficient WMPCs might be expected to exhibit impaired wnt signaling. In this regard, very high levels of the secreted WNT antagonist FRZB were also found in the WMPC pool (Table 1). FRZB has been shown to antagonize both WNT1 and WNT8 signaling (Wang et al., "Frzb, a Secreted Protein Expressed in the Spemann Organizer, Binds and Inhibits Wnt-8," *Cell* 88: 757-766 (1997); Leyns et al., "Frzb-1 is a Secreted Antagonist of Wnt Signaling Expressed in The Spemann Organizer," *Cell* 88: 747-756 (1997), which are hereby incorporated by reference in their entirety). The deficiency of RTPβ/ζ knock-out mice in remyelination, taken together with the tonic expression of both RTPβ/ζ and soluble frizzled by quiescent adult human WMPCs, may suggest a role for the RTPβ/ζ-dependent dephosphorylation of β-catenin in adult WMPCs. Taken together, these data suggest that RTPβ/ζ signaling is required for both maintaining and mobilizing glial progenitor cells in the adult human brain.

bpV(Phen) Inhibition of RTPβ/ζ Induced Oligodendrocyte Differentiation bpV(phen) is a potent inhibitor of tyrosine phosphatase activity (Posner et al., "Peroxovanadium Compounds. A New Class of Potent Phosphotyrosine Phosphatase Inhibitors Which Are Insulin Mimetics," J Biol Chem 269: 4596-4604 (1994); Faure et al., "Arrest at The G2/M Transition of the Cell Cycle by Protein-Tyrosine Phosphatase Inhibition: Studies on a Neuronal and a Glial Cell Line," *J Cell Biochem* 59: 389-401 (1995); Bevan et al., "Selective Activation of the Rat Hepatic Endosomal Insulin Receptor Kinase. Role for the Endosome in Insulin Signaling," *J Biol Chem* 270: 10784-10791 (1995), which are hereby incorporated by reference in their entirety). Although bpV(phen) inhibition has been shown to include a range of tyrosine phosphatase receptors (Bevan et al., "Selective Activation of the Rat Hepatic Endosomal Insulin Receptor Kinase. Role for the Endosome in Insulin Signaling," *J Biol Chem* 270: 10784-10791 (1995), which is hereby incorporated by reference in its entirety), RTPβ/ζ was by far the most significantly enriched receptor-encoding gene in the analysis, and no other receptor tyrosine phosphatases were identified as present in WMPC isolates. Thus, it would be expected that the inhibition of RTPβ/ζ was the specific incipient to oxovanadate-induced oligodendrocyte differentiation by cultured WMPCs.

Pleiotrophin Expression May Act as an Autocrine Brake Upon RTPβ/ζ Activity.

Pleiotrophin inhibits RTPβ/ζ dependent-dephosphorylation of β-catenin and, by so doing, antagonizes wnt signaling (Meng et al., "Pleiotrophin Signals Increased Tyrosine Phosphorylation of Beta Beta-Catenin Through Inactivation of the Intrinsic Catalytic Activity of the Receptor-Type Protein Tyrosine Phosphatase Beta/Zeta," *Proc Natl Acad Sci USA* 97: 2603-2608 (2000), which is hereby incorporated by reference in its entirety). Besides its strong differential expression, the microarray analyses also revealed a number of other in cis heterophilic ligands of RTPβ/ζ, such as NrCAM and the CSPGs, whose expression may serve to further modulate the phosphatase activity of RTPβ/ζ. This pattern of gene expression suggests that parallel pathways may operate to suppress wnt signaling in adult WMPCs. Since wnt signaling can actively drive neural progenitor expansion (Zechner et al., "Beta-Catenin Signals Regulate Cell Growth and the Balance Between Progenitor Cell Expansion and Differentiation in the Nervous System," *Dev Biol* 258: 406-418 (2003), which is hereby incorporated by reference in its entirety), the reversible inactivation of this pathway may be required for the maintenance of progenitors in a quiescent though mitotically competent state.

Syndecan and CASK-Dependent Signaling Comprise a Parallel Regulatory Pathway.

The present model accommodates the expression of syndecan-3 and its known binding partners, a number of which—including CASK, FGFR3, and PTN—were differentially expressed by adult WMPCs. Although syndecan-3 has been shown to act as a co-receptor for both PTN and FGF2, syndecan-3 can also transduce extracellular signals via ligand-induced, γ-secretase mediated proteolytic cleavage of its C-terminal C2 domain (Schulz et al., "Syndecan 3 Intramembrane Proteolysis is Presenilin/Gamma-Secretase-Dependent and Modulates Cytosolic Signaling," *J Biol Chem* (2003), which is hereby incorporated by reference in its entirety). In particular, release of the C-terminal domain frees the syndecan-3 bound protein calcium/calmodulin-activated serine kinase (CASK) to translocate to the nucleus, where it can act as a transcriptional activator through the T-box transcription factor TBR1, a brachyury family member (Hsueh et al., "Nuclear Translocation and Transcription Regulation by the Membrane-Associated Guanylate Kinase CASK/LIN-2," *Nature* 404: 298-302 (2000), which is hereby incorporated by reference in its entirety). Importantly, TBR1 was indeed present in the sorted WMPCs. Although the downstream targets of TBR1 and its family members are largely unknown, its induction may comprise another novel signaling pathway regulating the fate of adult WMPCs (FIG. 2).

Constitutive Activation of Notch Pathway.

The adult human WMPC resembles the rodent oligodendrocyte progenitor with regard to the notch signaling pathway (Wang et al., "Notch Receptor Activation Inhibits Oligodendrocyte Differentiation," *Neuron* 21: 63-75 (1998), which is hereby incorporated by reference in its entirety). WMPCs express high levels of both the notch receptor, NOTCH1, and its downstream effectors HES1 and musashi1. Indeed, the novel LIM-domain containing protein FHL1B, that appears to act downstream of notch to bind and transcriptionally activate RBP-J, was substantially enriched in WMPCs. Although the precise function of FHL1B in oligoneogenesis is unknown, it is worth noting that the developmental expression pattern of this gene clusters with that of the oligodendrocyte lineage markers PDGFαR, olig1 and olig2 during human fetal ventricular zone development. Furthermore, FHL1 expression has been described in microarray studies on skin, neural, hematopoietic, and embryonic stem cell populations suggesting a more widespread role of FHL1 in diverse stem and progenitor cell populations (Ramalho-Santos, et al., "Stemness: Transcriptional Profiling of Embryonic and Adult Stem Cells," *Science* 298: 597-600 (2002); Tumbar et al., "Defining the Epithelial Stem Cell Niche in Skin," *Science* 303: 359-363 (2004), which are hereby incorporated by reference in their entirety). Surprisingly, the notch ligand JAG1 was also differentially expressed by adult WMPCs. During development, oligodendrocyte progenitors do not appear to express jagged (Wang et al., "Notch Receptor Activation Inhibits Oligodendrocyte Differentiation," *Neuron* 21: 63-75 (1998), which is hereby incorporated by reference in its entirety). However, its expression by adult WMPCs may suggest a degree of lateral activation of notch signaling, that may serve to maintain contiguous progenitors in an undifferentiated state pending mobilization (John et al., "Multiple Sclerosis: Re-Expression of a Developmental Pathway That Restricts Oligodendrocyte Maturation," *Nature Med* 8: 1115-1121 (2002), which is hereby incorporated by reference in its entirety).

Notch signaling typically results in the up-regulation of HES1, which itself serves as a negative regulator of differentiation, as manifested by its repression of MASH1 and OLIG2 transcription. As a result, it was surprising to note the co-expression of MASH1 and HES1 by adult human WMPCs. Yet although the data suggests that MASH1 and HES1 are co-expressed by single cells, it might also be the case that the WMPC population contains multiple stages of parenchymal progenitor ontogeny.

The BMPs and their Antagonists.

BMP ligands can promote the differentiation of neural progenitor cells towards an astrocytic fate, and inhibit both neurogenesis and oligodendroglial differentiation (Gross et al., "Bone Morphogenetic Proteins Promote Astroglial Lineage Commitment by Mammalian Subventricular Zone Progenitor Cells," *Neuron* 17: 595-606 (1996); Mabie et al., "Bone Morphogenetic Proteins Induce Astroglial Differentiation of Oligodendroglial-Astroglial Progenitor Cells," *J Neurosci* 17: 4112-4120 (1997), which are hereby incorporated by reference in their entirety). It has been shown that when raised at low density and high purity, in the absence of either autocrine or paracrine growth factors, adult human WMPCs exhibit a pronounced neurogenic capacity, and are able to differentiate into functional neurons both in vitro and, upon transplantation, in vivo (Nunes et al., "Identification and Isolation of Multipotential Neural Progenitor Cells From the Subcortical White Matter of the Adult Human Brain," *Nat Med* 9: 439-447 (2003), which is hereby incorporated by reference in its entirety). In the present study, it has been shown that WMPCs express significantly more BMP2 and BMP7 than the surrounding white matter, while expressing both membrane-bound (BAMBI) and soluble (neuralin) inhibitors of other BMPs. Although the product of these combinatorial interactions remains unclear, together these observations suggest that tonically-expressed BMPs inhibit neurogenesis at high density in vitro, and may prevent neurogenesis from WMPCs in vivo.

Tyrosine Kinase Receptors.

Adult human WMPCs, like rat oligodendrocyte progenitors, respond to basic FGF as a mitogen, and suppress terminal differentiation (Roy et al., "Identification, Isolation, and Promoter-Defined Separation of Mitotic Oligodendrocyte Progenitor Cells From the Adult Human Subcortical White Matter," *J Neurosci* 19: 9986-95 (1999), which is hereby incorporated by reference in its entirety). The present data indicate that WMPCs express very high levels of the type 3 FGF receptor, compared to their parental white matter dissociate. Although FGFR3 has previously been shown to be expressed by astrocytes (Bansal et al., "Regulation of FGF Receptors in the Oligodendrocyte Lineage," *Mol Cell Neurosci* 7: 263-275 (1996), which is hereby incorporated by reference in its entirety), the high level of expression in WMPCs suggests this receptor may provide a important target for manipulation of WMPC proliferation in vitro and in vivo. Of the three identified endogenous ligands of FGFR3, FGF1 (acidic), FGF4 and FGF9, expression of FGF1 and FGF9 was detected in the microarrays (Chellaiah et al., "Fibroblast Growth Factor Receptor (FGFR) 3. Alternative Splicing in Immunoglobulin-Like Domain III Creates a Receptor Highly Specific for Acidic FGF/FGF-1," *J Biol Chem* 269: 11620-11627 (1994); Hecht et al., "Identification of Fibroblast Growth Factor 9 (FGF9) as a High Affinity, Heparin Dependent Ligand for FGF Receptors 3 and 2 but not for FGF Receptors 1 and 4," *Growth Factors* 12: 223-233 (1995); Ornitz et al., "Receptor Specificity of the Fibroblast Growth Factor Family," *J Biol Chem* 271: 15292-15297 (1996); Santos-Ocampo et al., "Expression and Biological Activity of Mouse Fibroblast Growth Factor-9," *J Biol Chem* 271: 1726-1731 (1996), which are hereby incorporated by reference in their entirety). While both FGF-1 & -9 have been shown to be mitogenic for A2B5-positive glial progenitors (Engele et al., "Effects of Acidic and Basic Fibroblast Growth Factors (aFGF, bFGF) on Glial Precursor Cell Proliferation: Age Dependency and Brain Region Specificity," *Dev Biol* 152: 363-372 (1992); Naruo et al., "Novel Secretory Heparin-Binding Factors From Human Glioma Cells (Glia-Activating Factors) Involved in Glial Cell Growth. Purification and Biological Properties," *J Biol Chem* 268: 2857-2864 (1993), which are hereby incorporated by reference in their entirety), only FGF-1 was significantly greater in the white matter dissociate than in the sorted WMPCs.

The PDGFαR was also highly expressed by WMPCs. PDGF is a mitogen for rodent and human glial progenitors, and can initiate oligodendrocytic differentiation. Moreover, PDGF signaling has been shown to induce pleiotrophin mRNA expression in 3T3 cells (Li et al., "Pleiotrophin Gene Expression is Highly Restricted and is Regulated by Platelet-Derived Growth Factor," *Biochem Biophys Res Commun* 184: 427-432 (1992), which is hereby incorporated by reference in its entirety). This suggests that PDGF signaling may induce oligodendrocyte commitment via autocrine PTN signaling on RTPβ/ζ and syndecan/CASK pathways (FIG. 2).

Overview

The differentially expressed transcripts of a highly enriched progenitor cell population isolated from the adult brain have been analyzed, and those transcripts were assessed in the context of complementary patterns of gene expression in the white matter environment. On that basis, a model for the pathways and interactions thereof by which glial progenitor cells are regulated in the adult human white matter has been established, and by which oligodendrocytic differentiation may be determined. At baseline, these interactions would appear to support the self-maintenance and turnover of WMPCs, while suppressing their directed differentiation. As the model of FIG. 2 illustrates, these pathways enjoy substantial cross-talk, which might both permit the system to respond readily to environmental change, while buffering it from perturbation by any single molecular stimulus. As such, these pathways may be targeted at a number of loci for genetic or pharmacological modulation of progenitor cell turnover and fate.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A method of increasing oligodendrocyte production from glial progenitor cells in a human subject, said method comprising:
    selecting an adult human subject requiring increased production of oligodendrocytes and
    administering, to the selected subject, an antagonist of receptor tyrosine phosphatase-β/ζ(RPTPZ), under conditions effective to increase, in the selected subject, oligodendrocyte production compared to oligodendrocyte production absent said administering.

2. The method of claim 1, wherein said antagonist of RPTPZ is selected from the group consisting of bpV (HOpic), bpV(phen), bpV(pic), CDC25 Phosphatase Inhibitor BN82002, DMHV, Dephostatin, 3,4-Dephostatin, Phenylarsine Oxide, Protein Tyrosine Phosphatase CD45 Inhibitor, Protein Tyrosine Phosphatase Inhibitor I, Protein Tyrosine Phosphatase Inhibitor II, Protein Tyrosine Phosphatase Inhibitor III, Protein Tyrosine Phosphatase Inhibitor IV, RK-682, Sodium Stibogluconate, and bpV(bipy).

3. A method of treating demyelination in a human subject, said method comprising:
    selecting an adult human subject with a condition characterized by demyelination and
    administering, to the selected subject, an antagonist of receptor tyrosine phosphatase-β/ζ(RPTPZ) under conditions effective to treat the demyelination in the human subject.

4. The method of claim 3, wherein said antagonist of RPTPZ is selected from the group consisting of bpV (HOpic), bpV(phen), bpV(pic), CDC25 Phosphatase Inhibitor BN82002, DMHV, Dephostatin, 3,4-Dephostatin, Phenylarsine Oxide, Protein Tyrosine Phosphatase CD45 Inhibitor, Protein Tyrosine Phosphatase Inhibitor I, Protein Tyrosine Phosphatase Inhibitor II, Protein Tyrosine Phosphatase Inhibitor III, Protein Tyrosine Phosphatase Inhibitor IV, RK-682, Sodium Stibogluconate, and bpV(bipy).

5. A method of treating a human subject for a condition characterized by underproduction, dysfunction, or loss of oligodendrocytes from human white matter, said method comprising:
    selecting an adult human subject with a condition characterized by underproduction, dysfunction, or loss of oligodendrocytes from human white matter and
    administering, to the selected subject, an antagonist of receptor tyrosine phosphatase-β/ζ(RPTPZ) under conditions effective to treat the condition characterized by underproduction, dysfunction, or loss of oligodendrocytes, wherein the condition is selected from the group consisting of inflammatory demyelination, radiation- or chemotherapy-induced white matter damage, and vascular demyelination.

6. The method of claim 5, wherein said antagonist of RPTPZ is selected from the group consisting of bpV (HOpic), bpV(phen), bpV(pic), CDC25 Phosphatase Inhibitor BN82002, DMHV, Dephostatin, 3,4-Dephostatin, Phenylarsine Oxide, Protein Tyrosine Phosphatase CD45 Inhibitor, Protein Tyrosine Phosphatase Inhibitor I, Protein Tyrosine Phosphatase Inhibitor II, Protein Tyrosine Phosphatase Inhibitor III, Protein Tyrosine Phosphatase Inhibitor IV, RK-682, Sodium Stibogluconate, and bpV(bipy).

* * * * *